United States Patent
Buchstaller

(10) Patent No.: US 11,261,185 B2
(45) Date of Patent: Mar. 1, 2022

(54) BICYCLIC HETEROCYCLIC DERIVATIVES

(71) Applicant: Merck Patent GmbH, Darmstadt (DE)

(72) Inventor: Hans-Peter Buchstaller, Griesheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 17/023,782

(22) Filed: Sep. 17, 2020

(65) Prior Publication Data

US 2021/0002278 A1   Jan. 7, 2021

Related U.S. Application Data

(62) Division of application No. 16/666,550, filed on Oct. 29, 2019, now Pat. No. 10,829,489, which is a division of application No. 15/748,786, filed as application No. PCT/EP2016/001114 on Jun. 30, 2016, now Pat. No. 10,526,325.

(30) Foreign Application Priority Data

Jul. 31, 2015   (EP) ..................... 15179210

(51) Int. Cl.
| | |
|---|---|
| *C07D 487/04* | (2006.01) |
| *C07D 471/04* | (2006.01) |
| *A61K 31/437* | (2006.01) |
| *A61K 31/4745* | (2006.01) |
| *A61P 35/00* | (2006.01) |

(52) U.S. Cl.
CPC .......... *C07D 471/04* (2013.01); *A61K 31/437* (2013.01); *A61K 31/4745* (2013.01); *A61P 35/00* (2018.01); *C07D 487/04* (2013.01)

(58) Field of Classification Search
CPC .................................................. C07D 487/04
See application file for complete search history.

(56) References Cited

U.S. PATENT DOCUMENTS

| | | | |
|---|---|---|---|
| 3,423,414 | A | 1/1969 | Blatter |
| 5,866,587 | A | 2/1999 | de Nanteuil et al. |
| 8,653,127 | B2 | 2/2014 | Luo |
| 8,691,838 | B2 | 4/2014 | Albrecht |
| 8,871,934 | B2 | 10/2014 | Motomura |
| 9,469,645 | B2 | 10/2016 | Chatterjee |
| 9,556,179 | B2 | 1/2017 | Velaparthi et al. |
| 9,676,784 | B2 | 6/2017 | Diaz-Fernández et al. |
| 9,751,861 | B2 | 9/2017 | Buchstaller |
| 9,963,454 | B2 | 5/2018 | Chatterjee et al. |

FOREIGN PATENT DOCUMENTS

| | | |
|---|---|---|
| CN | 1165817 A | 11/1997 |
| CN | 102471341 A | 5/2012 |
| EP | 2345629 A1 | 7/2011 |
| WO | 2009143477 A1 | 11/2009 |
| WO | 2010088050 A2 | 8/2010 |
| WO | 2011006143 A2 | 1/2011 |
| WO | 14100533 A1 | 6/2014 |
| WO | 15091795 A1 | 6/2015 |
| WO | 2015090496 A1 | 6/2015 |

OTHER PUBLICATIONS

International Search Report PCT/EP2016/001114 dated Aug. 2, 2016.
T.E. Roche et al., Cell. Mol. Life Sci., vol. 64, 2007, pp. 830-849.
A. Kumar et al., Chemico-Biological Interactions, vol. 199, 2012, pp. 29-37.
I. Papandreou et al., Int. J. Cancer, vol. 128, 2011, pp. 1001-1008.
G. Sutendra et al., Frontiers in Oncology, vol. 3, 2013, pp. 1-11.
Aicher et al: "Secondary amides of (R)-3,3,3-Trifluoro-2-hydroxo-2-methylpropionicacid as inhibitors of pyruvate dehydrogenase kinase", Journal of Medicinal Chemistry, American Chemical Society, US, vol. 43, No. 2, Jan. 27, 2000 (Jan. 27, 2000), pp. 236-249, XP002158429, ISSN: 0022-2623.
Wikipedia Pyruvate Dehydrogenase Kinase, retrieved Aug. 16, 2016.

*Primary Examiner* — Brian E McDowell
(74) *Attorney, Agent, or Firm* — Millen White Zelano & Branigan, PC; Brion P. Heaney

(57) ABSTRACT

Compounds of the formula Ia or of the formula Ib

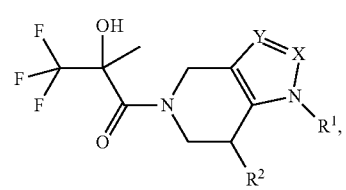

Ia

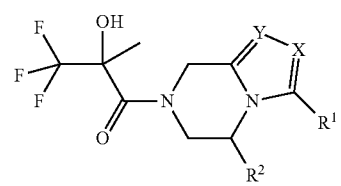

Ib in which X, Y, $R^1$ and $R^2$ have the meanings indicated in Claim 1, are inhibitors of pyruvate dehydrogenase kinase (PDHK), and can be employed, inter alia, for the treatment of diseases such as cancer.

15 Claims, No Drawings

BICYCLIC HETEROCYCLIC DERIVATIVES

TECHNICAL FIELD OF THE INVENTION

The present invention relates to novel bicyclic heterocyclic derivatives which inhibit pyruvate dehydrogenase kinase (PDHK), to pharmaceutical compositions comprising them, to processes for their preparation, and to their use in therapy for the treatment of cancers.

BACKGROUND OF THE INVENTION

Pyruvate dehydrogenase kinase (also pyruvate dehydrogenase complex kinase, PDC kinase, or PDHK) is a kinase enzyme which acts to inactivate the enzyme pyruvate dehydrogenase by phosphorylating it using ATP.

PDHK thus participates in the regulation of the pyruvate dehydrogenase complex of which pyruvate dehydrogenase is the first component. Both PDHK and the pyruvate dehydrogenase complex are located in the mitochondrial matrix of eukaryotes. The complex acts to convert pyruvate (a product of glycolysis in the cytosol) to acetyl-coA, which is then oxidized in the mitochondria to produce energy, in the citric acid cycle. By downregulating the activity of this complex, PDHK will decrease the oxidation of pyruvate in mitochondria and increase the conversion of pyruvate to lactate in the cytosol.

The opposite action of PDHK, namely the dephosphorylation and activation of pyruvate dehydrogenase, is catalyzed by a phosphoprotein phosphatase called pyruvate dehydrogenase phosphatase.

(Pyruvate dehydrogenase kinase should not be confused with Phosphoinositide-dependent kinase-1, which is also sometimes known as "PDK1".)

There are four known isozymes of PDHK in humans: PDHK1-PDHK4.

Some studies have shown that cells that lack insulin (or are insensitive to insulin) overexpress PDHK4. As a result, the pyruvate formed from glycolysis cannot be oxidized which leads to hyperglycaemia due to the fact that glucose in the blood cannot be used efficiently. Therefore several drugs target PDHK4 hoping to treat type II diabetes.

PDHK1 has shown to have increased activity in hypoxic cancer cells due to the presence of HIF-1. PDHK1 shunts pyruvate away from the citric acid cycle and keeps the hypoxic cell alive. Therefore, PDHK1 inhibition has been suggested as an antitumor therapy since PDHK1 prevents apoptosis in these cancerous cells. Similarly, PDHK3 has been shown to be overexpressed in colon cancer cell lines. Three proposed inhibitors are AZD7545 and dichloroacetate which both bind to PDHK1, and Radicicol which binds to PDHK3.

Increasing PDC in the active form by inhibiting PDHK activity is a drug target for diabetes, heart disease and cancer.

EP 2 345 629 A1 discloses PDHK inhibitors which are considered to be useful for the treatment or prophylaxis of diseases relating to glucose utilization disorder, for example, diabetes (e.g., type 1 diabetes, type 2 diabetes etc.), insulin resistance syndrome, metabolic syndrome, hyperglycemia and hyperlactacidemia. In addition, a PDHK inhibitor is considered to be useful for the treatment or prophylaxis of diabetic complications (e.g., neuropathy, retinopathy, nephropathy, cataract etc.). Furthermore, a PDHK inhibitor is considered to be useful for the treatment or prophylaxis of diseases caused by limited energy substrate supply to the tissues, for example, cardiac failure, cardiomyopathy, myocardial ischemia, dyslipidemia and atherosclerosis. Additionally, a PDHK inhibitor is considered to be useful for the treatment or prophylaxis of cerebral ischemia or cerebral apoplexy. Moreover, a PDHK inhibitor is considered to be useful for the treatment or prophylaxis of mitochondrial disease, mitochondrial encephalomyopathy, cancer and the like. Also, it is considered to be useful for the treatment or prophylaxis of pulmonary hypertension.

LITERATURE

Wikipedia, pyruvate dehydrogenase kinase;
T. E. Roche et al., Cell. Mol. Life Sci. 64 (2007) 830-849;
A. Kumar et al., Chemico-Biological Interactions 199 (2012) 29-37;
I. Papandreou et al., Int. J. Cancer: 128, 1001-1008 (2011);
G. Sutendra et al., frontiers in oncology, 2013, vol. 3, 1-11.

The invention had the object of finding novel compounds having valuable properties, in particular those which can be used for the preparation of medicaments.

It has been found that the compounds according to the invention and salts thereof have very valuable pharmacological properties while being well tolerated.

The present invention specifically relates to compounds of the formula Ia or Ib which inhibit PDHK, preferably PDHK2, to compositions which comprise these compounds, and to processes for the use thereof for the treatment of PDHK-induced diseases and complaints.

The compounds of the formula Ia or Ib can furthermore be used for the isolation and investigation of the activity or expression of PDHK. In addition, they are particularly suitable for use in diagnostic methods for diseases in connection with unregulated or disturbed PDHK activity.

The host or patient can belong to any mammalian species, for example a primate species, particularly humans; rodents, including mice, rats and hamsters; rabbits; horses, cows, dogs, cats, etc. Animal models are of interest for experimental investigations, providing a model for treatment of human disease.

The susceptibility of a particular cell to treatment with the compounds according to the invention can be determined by in vitro tests. Typically, a culture of the cell is combined with a compound according to the invention at various concentrations for a period of time which is sufficient to allow active agents such as anti IgM to induce a cellular response such as expression of a surface marker, usually between about one hour and one week. In vitro testing can be carried out using cultivated cells from blood or from a biopsy sample. The amount of surface marker expressed is assessed by flow cytometry using specific antibodies recognising the marker.

The dose varies depending on the specific compound used, the specific disease, the patient status, etc. A therapeutic dose is typically sufficient considerably to reduce the undesired cell population in the target tissue while the viability of the patient is maintained. The treatment is generally continued until a considerable reduction has occurred, for example an at least about 50% reduction in the cell burden, and may be continued until essentially no more undesired cells are detected in the body.

PRIOR ART

Bicylic pyrazolo-heterocyclic derivatives for the treatment of pain and inflammation are described in WO 2010/088050.

Other bicyclic heterocyclic compounds as protein kinase inhibitors are described in WO 2009/143477.

Other pyrazolopyridines for the treatment of inflammations are described in U.S. Pat. No. 3,423,414.

SUMMARY OF THE INVENTION

The invention relates to compounds of the formula Ia or of the formula Ib

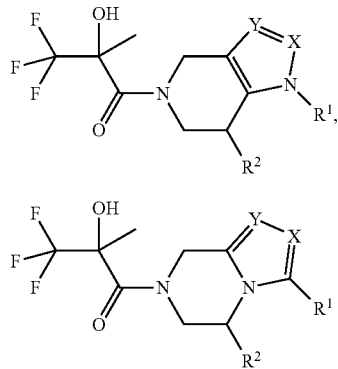

in which
X denotes CH or N,
Y denotes CH or N,
$R^1$ denotes H, A, $(CH_2)_nAr$, $(CH_2)_n$Het or Cyc,
$R^2$ denotes H or $CH_3$,
Ar denotes phenyl, which is unsubstituted or mono-, di-, tri-, tetra- or pentasubstituted by Hal, A, CN, OA, $[C(R^5)_2]_p$OH, $[C(R^5)_2]_pN(R^5)_2$, $NO_2$, $[C(R^5)_2]_p$COOR$^5$, $NR^5$COA, $NR^5SO_2A$, $[C(R^5)_2]_pSO_2N(R^5)_2$, $S(O)_nA$, $O[C(R^5)_2]_mN(R^5)_2$, $NR^5$COOA, $NR^5$CON($R^5$)$_2$ and/or COA,
Het denotes a mono- or bicyclic saturated, unsaturated or aromatic heterocycle having 1 to 4 N, O and/or S atoms, which is unsubstituted or mono- or disubstituted by Hal, A, CN, OA, $[C(R^5)_2]_p$OH, $[C(R^5)_2]_pN(R^5)_2$, $NO_2$, $[C(R^5)_2]_p$COOR$^5$, $NR^5$COA, $NR^5SO_2A$, $[C(R^5)_2]_pSO_2N(R^5)_2$, $S(O)_nA$, $O[C(R^5)_2]_mN(R^5)_2$, $NR^5$COOA, $NR^5$CON($R^5$)$_2$ and/or COA,
Cyc denotes cyclic alkyl with 3, 4, 5, 6 or 7 C-atoms, which is unsubstituted or monosubstituted by OH,
A denotes unbranched or branched alkyl with 1-10 C-atoms, wherein one or two non-adjacent CH- and/or CH$_2$-groups may be replaced by N-, O- and/or S-atoms and/or wherein 1-7 H-atoms may be replaced by $R^4$,
$R^4$ denotes F, Cl or OH,
$R^5$ denotes H oder A',
A' denotes unbranched or branched alkyl with 1-6 C-atoms, wherein 1-5 H-atoms may be replaced by F,
Hal denotes F, Cl, Br or I,
m denotes 1, 2, 3 or 4,
n denotes 0, 1 or 2,
p denotes 0, 1, 2, 3 or 4,
with the proviso that,
if X=CH then Y=N
or
if Y=CH then X=N,
and pharmaceutically acceptable salts, tautomers and stereoisomers thereof, including mixtures thereof in all ratios.

The invention also relates to the optically active forms (stereoisomers), the enantiomers, the racemates, the diastereomers and the hydrates and solvates of these compounds.

Moreover, the invention relates to pharmaceutically acceptable derivatives of compounds of formula Ia or Ib.

The term solvates of the compounds is taken to mean adductions of inert solvent molecules onto the compounds which form owing to their mutual attractive force. Solvates are, for example, mono- or dihydrates or alkoxides. It is understood, that the invention also relates to the solvates of the salts. The term pharmaceutically acceptable derivatives is taken to mean, for example, the salts of the compounds according to the invention and also so-called prodrug compounds.

As used herein and unless otherwise indicated, the term "prodrug" means a derivative of a compound of formula Ia or Ib that can hydrolyze, oxidize, or otherwise react under biological conditions (in vitro or in vivo) to provide an active compound, particularly a compound of formula Ia or Ib. Examples of prodrugs include, but are not limited to, derivatives and metabolites of a compound of formula Ia or Ib that include biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. In certain embodiments, prodrugs of compounds with carboxyl functional groups are the lower alkyl esters of the carboxylic acid. The carboxylate esters are conveniently formed by esterifying any of the carboxylic acid moieties present on the molecule. Prodrugs can typically be prepared using well-known methods, such as those described by Burger's Medicinal Chemistry and Drug Discovery 6th ed. (Donald J. Abraham ed., 2001, Wiley) and Design and Application of Prodrugs (H. Bundgaard ed., 1985, Harwood Academic Publishers Gmfh).

The expression "effective amount" denotes the amount of a medicament or of a pharmaceutical active ingredient which causes in a tissue, system, animal or human a biological or medical response which is sought or desired, for example, by a researcher or physician.

In addition, the expression "therapeutically effective amount" denotes an amount which, compared with a corresponding subject who has not received this amount, has the following consequence:
improved treatment, healing, prevention or elimination of a disease, syndrome, condition, complaint, disorder or side-effects or also the reduction in the advance of a disease, complaint or disorder.

The expression "therapeutically effective amount" also encompasses the amounts which are effective for increasing normal physiological function.

The invention also relates to the use of mixtures of the compounds of the formula Ia or Ib, for example mixtures of two diastereomers, for example in the ratio 1:1, 1:2, 1:3, 1:4, 1:5, 1:10, 1:100 or 1:1000.

These are particularly preferably mixtures of stereoisomeric compounds.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution.

The invention relates to the compounds of the formula Ia or Ib and salts thereof and to a process for the preparation of compounds of the formula Ia or Ib and pharmaceutically acceptable salts, solvates, tautomers and stereoisomers thereof characterised in that a compound of the formula IIa or IIb

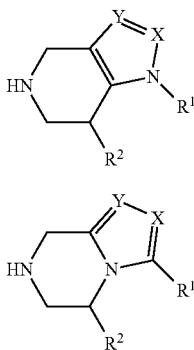

IIa

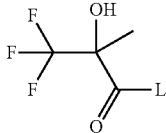

IIb in which X, Y, R¹ and R² have the meanings indicated in claim 1,
is reacted with a compound of the formula III

III in which L denotes Cl, Br, I or a free or reactively functionally modified OH group,
and/or
a base or acid of the formula I is converted into one of its salts.

Above and below, the radicals X, Y, R¹ and R² have the meanings indicated for the formula Ia or Ib, unless expressly stated otherwise.

A denotes alkyl, this is unbranched (linear) or branched, and has 1, 2, 3, 4, 5, 6, 7, 8, 9 or 10 C atoms. A preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A preferably denotes unbranched or branched alkyl with 1-10 C-atoms, wherein one or two non-adjacent CH- and/or CH₂-groups may be replaced by N- and/or O-atoms and wherein 1-7 H-atoms may be replaced by R⁴.

A very particularly preferably denotes alkyl having 1, 2, 3, 4, 5 or 6 C atoms, preferably methyl, ethyl, propyl, isopropyl, butyl, isobutyl, sec-butyl, tert-butyl, pentyl, hexyl, trifluoromethyl, pentafluoroethyl or 1,1,1-trifluoroethyl.

Moreover, A denotes preferably $CH_2OCH_3$, $CH_2CH_2OH$ or $CH_2CH_2OCH_3$. Cyc denotes cyclopropyl, cyclobutyl, cyclopentyl, cyclohexyl or cycloheptyl, preferably unsubstituted or monosubstituted by OH.

A' denotes alkyl, this is unbranched (linear) or branched, and has 1, 2, 3, 4, 5 or 6 C atoms. A' preferably denotes methyl, furthermore ethyl, propyl, isopropyl, butyl, isobutyl, sec-butyl or tert-butyl, furthermore also pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl, 1,1,2- or 1,2,2-trimethylpropyl, furthermore preferably, for example, trifluoromethyl.

A' very particularly preferably denotes alkyl having 1, 2, 3, 4, 5 or 6 C atoms, wherein 1-3 H-atoms may be replaced by F.

Ar denotes preferably o-, m- or p-tolyl, o-, m- or p-ethylphenyl, o-, m- or p-propylphenyl, o-, m- or p-isopropylphenyl, o-, m- or p-tert-butylphenyl, o-, m- or p-hydroxyphenyl, o-, m- or p-nitrophenyl, o-, m- or p-aminophenyl, o-, m- or p-(N-methylamino)phenyl, o-, m- or p-(N-methylaminocarbonyl)phenyl, o-, m- or p-methoxyphenyl, o-, m- or p-ethoxyphenyl, o-, m- or p-ethoxycarbonyl-phenyl, o-, m- or p-(N,N-dimethylamino)phenyl, o-, m- or p-(N,N-dimethyl-aminocarbonyl)phenyl, o-, m- or p-(N-ethylamino)phenyl, o-, m- or p-(N,N-diethylamino)phenyl, o-, m- or p-fluorophenyl, o-, m- or p-bromophenyl, o-, m- or p-chlorophenyl, o-, m- or p-(methylsulfonamido)phenyl, o-, m- or p-(methyl-sulfonyl)phenyl, o-, m- or p-cyanophenyl, o-, m- or p-carboxyphenyl, o-, m- or p-methoxycarbonylphenyl, o-, m- or p-acetylphenyl, o-, m- or p-amino-sulfonylphenyl, o-, m- or p-[2-(morpholin-4-yl)ethoxy]phenyl, o-, m- or p-[3-(N,N-diethylamino)propoxy]phenyl, furthermore preferably 2,3-, 2,4-, 2,5-, 2,6-, 3,4- or 3,5-difluorophenyl, 2,3-, 2,4-, 2,5-, 2,6-, 3,4- or 3,5-dichlorophenyl, 2,3-, 2,4-, 2,5-, 2,6-, 3,4- or 3,5-dibromophenyl, 2,4- or 2,5-dinitrophenyl, 2,5- or 3,4-dimethoxyphenyl, 3-nitro-4-chlorophenyl, 3-amino-4-chloro-, 2-amino-3-chloro-, 2-amino-4-chloro-, 2-amino-5-chloro- or 2-amino-6-chlorophenyl, 2-nitro-4-N,N-dimethylamino- or 3-nitro-4-N,N-dimethylaminophenyl, 2,3-diaminophenyl, 2,3,4-, 2,3,5-, 2,3,6-, 2,4,6- or 3,4,5-trichlorophenyl, 2,4,6-trimethoxyphenyl, 2-hydroxy-3,5-dichlorophenyl, p-iodophenyl, 3,6-dichloro-4-aminophenyl, 4-fluoro-3-chlorophenyl, 2-fluoro-4-bromophenyl, 2,5-difluoro-4-bromophenyl, 3-bromo-6-methoxyphenyl, 3-chloro-6-methoxyphenyl, 3-chloro-4-acetamidophenyl, 3-fluoro-4-methoxyphenyl, 3-amino-6-methylphenyl, 3-chloro-4-acetamidophenyl or 2,5-dimethyl-4-chlorophenyl.

Ar furthermore preferably denotes phenyl, which is unsubstituted or mono-, di-, tri-, tetra- or pentasubstituted by Hal, A, CN and/or OA.

Irrespective of further substitutions, Het denotes, for example, 2- or 3-furyl, 2- or 3-thienyl, 1-, 2- or 3-pyrrolyl, 1-, 2, 4- or 5-imidazolyl, 1-, 3-, 4- or 5-pyrazolyl, 2-, 4- or 5-oxazolyl, 3-, 4- or 5-isoxazolyl, 2-, 4- or 5-thiazolyl, 3-, 4- or 5-isothiazolyl, 2-, 3- or 4-pyridyl, 2-, 4-, 5- or 6-pyrimidinyl, furthermore preferably 1,2,3-triazol-1-, -4- or -5-yl, 1,2,4-triazol-1-, -3- or 5-yl, 1- or 5-tetrazolyl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 1,2,3-thiadiazol-4- or -5-yl, 3- or 4-pyridazinyl, pyrazinyl, 1-, 2-, 3-, 4-, 5-, 6- or 7-indolyl, 4- or 5-isoindolyl, indazolyl, 1-, 2-, 4- or 5-benzimidazolyl, 1-, 3-, 4-, 5-, 6- or 7-benzopyrazolyl, 2-, 4-, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6- or 7-benz-2,1,3-oxadiazolyl, 2-, 3-, 4-, 5-, 6-, 7- or 8-quinolyl, 1-, 3-, 4-, 5-, 6-, 7- or 8-isoquinolyl, 3-, 4-, 5-, 6-, 7- or 8-cinnolinyl, 2-, 4-, 5-, 6-, 7- or 8-quinazolinyl, 5- or 6-quinoxalinyl, 2-, 3-, 5-, 6-, 7- or 8-2H-benzo-1,4-oxazinyl, further preferably 1,3-benzodioxol-5-yl, 1,4-benzodioxan-6-yl, 2,1,3-benzothiadiazol-4-, -5-yl or 2,1,3-benzoxadiazol-5-yl, azabicyclo[3.2.1]octyl or dibenzofuranyl.

The heterocyclic radicals may also be partially or fully hydrogenated. Irrespective of further substitutions, Het can thus also denote, for example, 2,3-dihydro-2-, -3-, -4- or -5-furyl, 2,5-dihydro-2-, -3-, -4- or 5-furyl, tetrahydro-2- or -3-furyl, 1,3-dioxolan-4-yl, tetrahydro-2- or -3-thienyl, 2,3-dihydro-1-, -2-, -3-, -4- or -5-pyrrolyl, 2,5-dihydro-1-, -2-, -3-, -4- or -5-pyrrolyl, 1-, 2- or 3-pyrrolidinyl, tetrahydro-1-, -2- or -4-imidazolyl, 2,3-dihydro-1-, -2-, -3-, -4- or -5-pyrazolyl, tetrahydro-1-, -3- or 4-pyrazolyl, 1,4-dihydro-1-, -2-, -3- or -4-pyridyl, 1,2,3,4-tetrahydro-1-, -2-, -3-, -4-, -5- or -6-pyridyl, 1-, 2-, 3- or 4-piperidinyl, 2-, 3- or 4-morpholinyl, tetrahydro-2-, -3- or -4-pyranyl, 1,4-dioxanyl, 1,3-dioxan-2-, -4- or -5-yl, hexahydro-1-, -3- or -4-pyridazinyl, hexahydro-1-, -2-, -4- or -5-pyrimidinyl, 1-, 2- or 3-piperazinyl, 1,2,3,4-tetrahydro-1-, -2-, -3-, -4-, -5-, -6-, -7- or -8-quinolyl, 1,2,3,4-tetrahydro-1-, -2-, -3-, -4-, -5-, -6-, -7- or -8-isoquinolyl, 2-, 3-, 5-, 6-, 7- or 8-3,4-dihydro-2H-benzo-1,4-oxazinyl, furthermore preferably 2,3-methylenedioxyphenyl, 3,4-methylenedioxyphenyl, 2,3-ethylenedioxyphenyl, 3,4-ethylenedioxyphenyl, 3,4-(difluoromethylenedioxy)phenyl, 2,3-dihydrobenzofuran-5- or 6-yl, 2,3-(2-oxomethylenedioxy)phenyl or also 3,4-dihydro-2H-1,5-benzodioxepin-6- or -7-yl, furthermore preferably 2,3-dihydrobenzofuranyl, 2,3-dihydro-2-oxofuranyl, 3,4-dihydro-2-oxo-1H-quinazolinyl, 2,3-dihydrobenzoxazolyl, 2-oxo-2,3-dihydrobenzoxazolyl, 2,3-dihydrobenzimidazolyl, 1,3-dihydroindole, 2-oxo-1,3-dihydroindole or 2-oxo-2,3-dihydrobenzimidazolyl.

Het preferably denotes pyrimidyl, pyridyl, pyridazinyl, pyrazinyl, piperidinyl, pyrrolidinyl, pyrazolyl, thiazolyl, imidazolyl, furanyl, thiophenyl, pyrrolyl, oxazolyl, isoxazolyl, triazolyl, oxadiazolyl or thiadiazolyl, each of which is unsubstituted or mono- or disubstituted by Hal, A and/or OA.

Hal preferably denotes F, Cl or Br, but also I, particularly preferably F or Cl.

Throughout the invention, all radicals which occur more than once may be identical or different, i.e. are independent of one another.

The compounds of the formula Ia or Ib may have one or more chiral centres and can therefore occur in various stereoisomeric forms. The formula Ia or Ib encompasses all these forms.

Accordingly, the invention relates, in particular, to the compounds of the formula Ia or Ib in which at least one of the said radicals has one of the preferred meanings indicated above. Some preferred groups of compounds may be expressed by the following sub-formulae Iaa to Iac, which conform to the formula Ia or Ib and in which the radicals not designated in greater detail have the meaning indicated for the formula Ia or Ib, but in which in Iaa Ar denotes phenyl, which is unsubstituted or mono-, di-, tri-, tetra- or pentasubstituted by Hal, A, CN and/or OA;

in Iab Het denotes pyrimidyl, pyridyl, pyridazinyl, pyrazinyl, piperidinyl, pyrrolidinyl, pyrazolyl, thiazolyl, imidazolyl, furanyl, thiophenyl, pyrrolyl, oxazolyl, isoxazolyl, triazolyl, oxadiazolyl or thiadiazolyl, each of which is unsubstituted or mono- or disubstituted by Hal, A and/or OA;

in Iac X denotes CH or N,
Y denotes CH or N,
$R^1$ denotes H, A, $(CH_2)_n Ar$, $(CH_2)_n Het$ or Cyc,
$R^2$ denotes H or $CH_3$,
Ar denotes phenyl, which is unsubstituted or mono-, di-, tri-, tetra- or pentasubstituted by Hal, A, CN and/or OA,
Het denotes pyrimidyl, pyridyl, pyridazinyl, pyrazinyl, piperidinyl, pyrrolidinyl, pyrazolyl, thiazolyl, imidazolyl, furanyl, thiophenyl, pyrrolyl, oxazolyl, isoxazolyl, triazolyl, oxadiazolyl or thiadiazolyl, each of which is unsubstituted or mono- or disubstituted by Hal, A and/or OA,
Cyc denotes cyclic alkyl with 3, 4, 5, 6 or 7 C-atoms, which is unsubstituted or monosubstituted by OH,
A denotes unbranched or branched alkyl with 1-10 C-atoms, wherein one or two non-adjacent CH- and/or $CH_2$-groups may be replaced by N-, O- and/or S-atoms and/or wherein 1-7 H-atoms may be replaced by $R^4$,
$R^4$ denotes F, Cl or OH,
Hal denotes F, Cl, Br or I,
n denotes 0, 1 or 2,
with the proviso that,
if X=CH then Y=N
or d
if Y=CH then X=N,
and pharmaceutically acceptable salts, tautomers and stereoisomers thereof, including mixtures thereof in all ratios.

The compounds of the formula Ia or Ib and also the starting materials for their preparation are, in addition, prepared by methods known per se, as described in the literature (for example in the standard works, such as Houben-Weyl, Methoden der organischen Chemie [Methods of Organic Chemistry], Georg-Thieme-Verlag, Stuttgart), to be precise under reaction conditions which are known and suitable for the said reactions. Use can also be made here of variants known per se which are not mentioned here in greater detail.

The starting compounds for the preparation of compounds of formula Ia or Ib are generally known. If they are novel, however, they can be prepared by methods known per se.

Compounds of the formula Ia or Ib can preferably be obtained by reacting a compound of the formula IIa or IIb, with a compound of the formula III.

In the compounds of the formula III, L preferably denotes Cl, Br, I or a free or reactively modified OH group, such as, for example, an activated ester, an imidazolide or alkylsulfonyloxy having 1-6 C atoms (preferably methyl-sulfonyloxy or trifluoromethylsulfonyloxy) or arylsulfonyloxy having 6-10 C atoms (preferably phenyl- or p-tolylsulfonyloxy).

The reaction is generally carried out in the presence of an acid-binding agent, preferably an organic base, such as DIPEA, triethylamine, dimethyl-aniline, pyridine or quinoline.

The addition of an alkali or alkaline earth metal hydroxide, carbonate or bicarbonate or another salt of a weak acid of the alkali or alkaline earth metals, preferably of potassium, sodium, calcium or caesium, may also be favourable.

Preferably the reaction is carried out in the presence of [Dimethylamino-([1,2,3]triazolo[4,5-b]pyridin-3-yloxy)-methylene]-dimethyl-ammonium hexafluoro phosphate [HATU; coupling reagent] or in the presence of 1-chloro-N,N,2-trimethyl-1-propenylamine.

Depending on the conditions used, the reaction time is between a few minutes and 14 days, the reaction temperature is between about −30° and 140°, normally between −10° and 90°, in particular between about 0° and about 70°.

Examples of suitable inert solvents are hydrocarbons, such as hexane, petroleum ether, benzene, toluene or xylene; chlorinated hydrocarbons, such as trichloroethylene, 1,2-dichloroethane, carbon tetrachloride, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether, ethylene glycol dimethyl ether (diglyme); ketones, such as acetone or butanone; amides, such as acetamide, dimethylacetamide or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Particular preference is given to acetonitrile, dichloromethane and/or DMF.

Pharmaceutical Salts and Other Forms

The said compounds according to the invention can be used in their final non-salt form. On the other hand, the present invention also encompasses the use of these compounds in the form of their pharmaceutically acceptable salts, which can be derived from various organic and inorganic acids and bases by procedures known in the art. Pharmaceutically acceptable salt forms of the compounds of the formula Ia or Ib are for the most part prepared by conventional methods. If the compound of the formula Ia or Ib contains a carboxyl group, one of its suitable salts can be formed by reacting the compound with a suitable base to give the corresponding base-addition salt. Such bases are, for example, alkali metal hydroxides, including potassium hydroxide, sodium hydroxide and lithium hydroxide; alkaline earth metal hydroxides, such as barium hydroxide and calcium hydroxide; alkali metal alkoxides, for example potassium ethoxide and sodium propoxide; and various organic bases, such as piperidine, diethanolamine and N-methylglutamine. The aluminium salts of the compounds of the formula Ia or Ib are likewise included. In the case of certain compounds of the formula Ia or Ib, acid-addition salts can be formed by treating these compounds with pharmaceutically acceptable organic and inorganic acids, for example hydrogen halides, such as hydrogen chloride, hydrogen bromide or hydrogen iodide, other mineral acids and corresponding salts thereof, such as sulfate, nitrate or phosphate and the like, and alkyl- and monoarylsulfonates, such as ethanesulfonate, toluenesulfonate and benzenesulfonate, and other organic acids and corresponding salts thereof, such as acetate, trifluoroacetate, tartrate, maleate, succinate, citrate, benzoate, salicylate, ascorbate and the like. Accordingly, pharmaceutically acceptable acid-addition salts of the compounds of the formula Ia or Ib include the following: acetate, adipate, alginate, arginate, aspartate, benzoate, benzene-sulfonate (besylate), bisulfate, bisulfite, bromide, butyrate, camphorate, camphorsulfonate, caprylate, chloride, chlorobenzoate, citrate, cyclopentane-propionate, digluconate, dihydrogenphosphate, dinitrobenzoate, dodecyl-sulfate, ethanesulfonate, fumarate, formate, galacterate (from mucic acid), galacturonate, glucoheptanoate, gluconate, glutamate, glycerophosphate, hemisuccinate, hemisulfate, heptanoate, hexanoate, hippurate, hydrochloride, hydrobromide, hydroiodide, 2-hydroxyethanesulfonate, iodide, isethionate, iso-butyrate, lactate, lactobionate, malate, maleate, malonate, mandelate, metaphosphate, methanesulfonate, methylbenzoate, monohydrogenphosphate, 2-naphthalenesulfonate, nicotinate, nitrate, oxalate, oleate, palmoate, pectinate, persulfate, phenylacetate, 3-phenylpropionate, phosphate, phosphonate, phthalate, but this does not represent a restriction.

Furthermore, the base salts of the compounds according to the invention include aluminium, ammonium, calcium, copper, iron(III), iron(II), lithium, magnesium, manganese (III), manganese(II), potassium, sodium and zinc salts, but this is not intended to represent a restriction. Of the above-mentioned salts, preference is given to ammonium; the alkali metal salts sodium and potassium, and the alkaline earth metal salts calcium and magnesium. Salts of the compounds of the formula Ia or Ib which are derived from pharmaceutically acceptable organic non-toxic bases include salts of primary, secondary and tertiary amines, substituted amines, also including naturally occurring substituted amines, cyclic amines, and basic ion exchanger resins, for example arginine, betaine, caffeine, chloroprocaine, choline, N,N'-dibenzylethylenediamine (benzathine), dicyclohexylamine, diethanolamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lidocaine, lysine, meglumine, N-methyl-D-glucamine, morpholine, piperazine, piperidine, polyamine resins, procaine, purines, theobromine, triethanolamine, triethylamine, trimethylamine, tripropylamine and tris(hydroxymethyl)methylamine (tromethamine), but this is not intended to represent a restriction.

Compounds of the present invention which contain basic nitrogen-containing groups can be quaternised using agents such as $(C_1-C_4)$alkyl halides, for example methyl, ethyl, isopropyl and tert-butyl chloride, bromide and iodide; di($C_1$-$C_4$)alkyl sulfates, for example dimethyl, diethyl and diamyl sulfate; $(C_{10}-C_{18})$alkyl halides, for example decyl, dodecyl, lauryl, myristyl and stearyl chloride, bromide and iodide; and aryl($C_1-C_4$)alkyl halides, for example benzyl chloride and phenethyl bromide. Both water- and oil-soluble compounds according to the invention can be prepared using such salts.

The above-mentioned pharmaceutical salts which are preferred include acetate, trifluoroacetate, besylate, citrate, fumarate, gluconate, hemisuccinate, hippurate, hydrochloride, hydrobromide, isethionate, mandelate, meglumine, nitrate, oleate, phosphonate, pivalate, sodium phosphate, stearate, sulfate, sulfosalicylate, tartrate, thiomalate, tosylate and tromethamine, but this is not intended to represent a restriction.

Particular preference is given to hydrochloride, dihydrochloride, hydrobromide, maleate, mesylate, phosphate, sulfate and succinate.

The acid-addition salts of basic compounds of the formula Ia or Ib are prepared by bringing the free base form into contact with a sufficient amount of the desired acid, causing the formation of the salt in a conventional manner. The free base can be regenerated by bringing the salt form into contact with a base and isolating the free base in a conventional manner. The free base forms differ in a certain respect from the corresponding salt forms thereof with respect to certain physical properties, such as solubility in polar solvents; for the purposes of the invention, however, the salts otherwise correspond to the respective free base forms thereof.

As mentioned, the pharmaceutically acceptable base-addition salts of the compounds of the formula Ia or Ib are formed with metals or amines, such as alkali metals and alkaline earth metals or organic amines. Preferred metals are sodium, potassium, magnesium and calcium. Preferred organic amines are N,N'-dibenzylethylenediamine, chloroprocaine, choline, diethanolamine, ethylenediamine, N-methyl-D-glucamine and procaine.

The base-addition salts of acidic compounds according to the invention are prepared by bringing the free acid form into contact with a sufficient amount of the desired base, causing the formation of the salt in a conventional manner. The free acid can be regenerated by bringing the salt form into contact with an acid and isolating the free acid in a conventional manner. The free acid forms differ in a certain respect from the corresponding salt forms thereof with respect to certain physical properties, such as solubility in polar solvents; for the purposes of the invention, however, the salts otherwise correspond to the respective free acid forms thereof.

If a compound according to the invention contains more than one group which is capable of forming pharmaceutically acceptable salts of this type, the invention also encompasses multiple salts. Typical multiple salt forms include, for example, bitartrate, diacetate, difumarate, dimeglumine, diphosphate, disodium and trihydrochloride, but this is not intended to represent a restriction.

With regard to that stated above, it can be seen that the expression "pharmaceutically acceptable salt" in the present connection is taken to mean an active ingredient which comprises a compound of the formula Ia or Ib in the form of one of its salts, in particular if this salt form imparts improved pharmacokinetic properties on the active ingredient compared with the free form of the active ingredient or any other salt form of the active ingredient used earlier. The pharmaceutically acceptable salt form of the active ingredient can also provide this active ingredient for the first time with a desired pharmacokinetic property which it did not have earlier and can even have a positive influence on the pharmacodynamics of this active ingredient with respect to its therapeutic efficacy in the body.

Isotopes

There is furthermore intended that a compound of the formula Ia or Ib includes isotope-labelled forms thereof. An isotope-labelled form of a compound of the formula Ia or Ib is identical to this compound apart from the fact that one or more atoms of the compound have been replaced by an atom or atoms having an atomic mass or mass number which differs from the atomic mass or mass number of the atom which usually occurs naturally. Examples of isotopes which are readily commercially available and which can be incorporated into a compound of the formula I by well-known methods include isotopes of hydrogen, carbon, nitrogen, oxygen, phosphorus, fluorine and chlorine, for example $^2H$, $^3H$, $^{13}C$, $^{14}C$, $^{15}N$, $^{18}O$, $^{17}O$, $^{31}P$, $^{32}P$, $^{35}S$, $^{18}F$ and $^{36}Cl$, respectively. A compound of the formula Ia or Ib, a prodrug, thereof or a pharmaceutically acceptable salt of either which contains one or more of the above-mentioned isotopes and/or other isotopes of other atoms is intended to be part of the present invention. An isotope-labelled compound of the formula Ia or Ib can be used in a number of beneficial ways. For example, an isotope-labelled compound of the formula Ia or Ib into which, for example, a radioisotope, such as $^3H$ or $^{14}C$, has been incorporated is suitable for medicament and/or substrate tissue distribution assays. These radioisotopes, i.e. tritium ($^3H$) and carbon-14 ($^{14}C$), are particularly preferred owing to simple preparation and excellent detectability. Incorporation of heavier isotopes, for example deuterium ($^2H$), into a compound of the formula Ia or Ib has therapeutic advantages owing to the higher metabolic stability of this isotope-labelled compound. Higher metabolic stability translates directly into an increased in vivo half-life or lower dosages, which under most circumstances would represent a preferred embodiment of the present invention. An isotope-labelled compound of the formula Ia or Ib can usually be prepared by carrying out the procedures disclosed in the synthesis schemes and the related description, in the example part and in the preparation part in the present text, replacing a non-isotope-labelled reactant by a readily available isotope-labelled reactant.

Deuterium ($^2H$) can also be incorporated into a compound of the formula Ia or Ib for the purpose in order to manipulate the oxidative metabolism of the compound by way of the primary kinetic isotope effect. The primary kinetic isotope effect is a change of the rate for a chemical reaction that results from exchange of isotopic nuclei, which in turn is caused by the change in ground state energies necessary for covalent bond formation after this isotopic exchange. Exchange of a heavier isotope usually results in a lowering of the ground state energy for a chemical bond and thus cause a reduction in the rate in rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_M/k_D=2-7$ are typical. If this rate difference is successfully applied to a compound of the formula Ia or Ib that is susceptible to oxidation, the profile of this compound in vivo can be drastically modified and result in improved pharmacokinetic properties.

When discovering and developing therapeutic agents, the person skilled in the art attempts to optimise pharmacokinetic parameters while retaining desirable in vitro properties. It is reasonable to assume that many compounds with poor pharmacokinetic profiles are susceptible to oxidative metabolism. In vitro liver microsomal assays currently available provide valuable information on the course of oxidative metabolism of this type, which in turn permits the rational design of deuterated compounds of the formula Ia or Ib with improved stability through resistance to such oxidative metabolism. Significant improvements in the pharmacokinetic profiles of compounds of the formula Ia or Ib are thereby obtained, and can be expressed quantitatively in terms of increases in the in vivo half-life (t½), concentration at maximum therapeutic effect ($C_{max}$), area under the dose response curve (AUC), and F; and in terms of reduced clearance, dose and materials costs.

The following is intended to illustrate the above: a compound of the formula Ia or Ib which has multiple potential sites of attack for oxidative metabolism, for example benzylic hydrogen atoms and hydrogen atoms bonded to a nitrogen atom, is prepared as a series of analogues in which various combinations of hydrogen atoms are replaced by deuterium atoms, so that some, most or all of these hydrogen atoms have been replaced by deuterium atoms. Half-life determinations enable favourable and accurate determination of the extent of the extent to which the improvement in resistance to oxidative metabolism has improved. In this way, it is determined that the half-life of the parent compound can be extended by up to 100% as the result of deuterium-hydrogen exchange of this type.

Deuterium-hydrogen exchange in a compound of the formula Ia or Ib can also be used to achieve a favourable modification of the metabolite spectrum of the starting compound in order to diminish or eliminate undesired toxic metabolites. For example, if a toxic metabolite arises through oxidative carbon-hydrogen (C—H) bond cleavage, it can reasonably be assumed that the deuterated analogue will greatly diminish or eliminate production of the unwanted metabolite, even if the particular oxidation is not a rate-determining step. Further information on the state of the art with respect to deuterium-hydrogen exchange may be found, for example in Hanzlik et al., J. Org. Chem. 55, 3992-3997, 1990, Reider et al., J. Org. Chem. 52, 3326-3334, 1987, Foster, Adv. Drug Res. 14, 1-40, 1985, Gillette et al, Biochemistry 33(10) 2927-2937, 1994, and Jarman et al. Carcinogenesis 16(4), 683-688, 1993.

The invention furthermore relates to medicaments comprising at least one compound of the formula Ia or Ib and/or pharmaceutically acceptable salts, tautomers and stereoisomers thereof, including mixtures thereof in all ratios, and optionally excipients and/or adjuvants.

Pharmaceutical formulations can be administered in the form of dosage units which comprise a predetermined amount of active ingredient per dosage unit. Such a unit can comprise, for example, 0.5 mg to 1 g, preferably 1 mg to 700 mg, particularly preferably 5 mg to 100 mg, of a compound according to the invention, depending on the condition treated, the method of administration and the age, weight and condition of the patient, or pharmaceutical formulations can be administered in the form of dosage units which comprise a predetermined amount of active ingredient per dosage unit. Preferred dosage unit formulations are those which comprise a daily dose or part-dose, as indicated above, or a corresponding fraction thereof of an active ingredient.

Furthermore, pharmaceutical formulations of this type can be prepared using a process which is generally known in the pharmaceutical art.

Pharmaceutical formulations can be adapted for administration via any desired suitable method, for example by oral (including buccal or sublingual), rectal, nasal, topical (including buccal, sublingual or transdermal), vaginal or parenteral (including subcutaneous, intramuscular, intravenous or intradermal) methods. Such formulations can be prepared using all processes known in the pharmaceutical art by, for example, combining the active ingredient with the excipient(s) or adjuvant(s).

Pharmaceutical formulations adapted for oral administration can be administered as separate units, such as, for example, capsules or tablets; powders or granules; solutions or suspensions in aqueous or non-aqueous liquids; edible foams or foam foods; or oil-in-water liquid emulsions or water-in-oil liquid emulsions.

Thus, for example, in the case of oral administration in the form of a tablet or capsule, the active-ingredient component can be combined with an oral, non-toxic and pharmaceutically acceptable inert excipient, such as, for example, ethanol, glycerol, water and the like. Powders are prepared by comminuting the compound to a suitable fine size and mixing it with a pharmaceutical excipient comminuted in a similar manner, such as, for example, an edible carbohydrate, such as, for example, starch or mannitol. A flavour, preservative, dispersant and dye may likewise be present.

Capsules are produced by preparing a powder mixture as described above and filling shaped gelatine shells therewith. Glidants and lubricants, such as, for example, highly disperse silicic acid, talc, magnesium stearate, calcium stearate or polyethylene glycol in solid form, can be added to the powder mixture before the filling operation. A disintegrant or solubiliser, such as, for example, agar-agar, calcium carbonate or sodium carbonate, may likewise be added in order to improve the availability of the medicament after the capsule has been taken.

In addition, if desired or necessary, suitable binders, lubricants and disintegrants as well as dyes can likewise be incorporated into the mixture. Suitable binders include starch, gelatine, natural sugars, such as, for example, glucose or beta-lactose, sweeteners made from maize, natural and synthetic rubber, such as, for example, acacia, tragacanth or sodium alginate, carboxymethylcellulose, polyethylene glycol, waxes, and the like. The lubricants used in these dosage forms include sodium oleate, sodium stearate, magnesium stearate, sodium benzoate, sodium acetate, sodium chloride and the like. The disintegrants include, without being restricted thereto, starch, methylcellulose, agar, bentonite, xanthan gum and the like. The tablets are formulated by, for example, preparing a powder mixture, granulating or dry-pressing the mixture, adding a lubricant and a disintegrant and pressing the entire mixture to give tablets. A powder mixture is prepared by mixing the compound comminuted in a suitable manner with a diluent or a base, as described above, and optionally with a binder, such as, for example, carboxymethylcellulose, an alginate, gelatine or polyvinylpyrrolidone, a dissolution retardant, such as, for example, paraffin, an absorption accelerator, such as, for example, a quaternary salt, and/or an absorbent, such as, for example, bentonite, kaolin or dicalcium phosphate. The powder mixture can be granulated by wetting it with a binder, such as, for example, syrup, starch paste, acadia mucilage or solutions of cellulose or polymer materials and pressing it through a sieve. As an alternative to granulation, the powder mixture can be run through a tabletting machine, giving lumps of non-uniform shape, which are broken up to form granules. The granules can be lubricated by addition of stearic acid, a stearate salt, talc or mineral oil in order to prevent sticking to the tablet casting moulds. The lubricated mixture is then pressed to give tablets. The compounds according to the invention can also be combined with a free-flowing inert excipient and then pressed directly to give tablets without carrying out the granulation or dry-pressing steps. A transparent or opaque protective layer consisting of a shellac sealing layer, a layer of sugar or polymer material and a gloss layer of wax may be present. Dyes can be added to these coatings in order to be able to differentiate between different dosage units.

Oral liquids, such as, for example, solution, syrups and elixirs, can be prepared in the form of dosage units so that a given quantity comprises a pre-specified amount of the compound. Syrups can be prepared by dissolving the compound in an aqueous solution with a suitable flavour, while elixirs are prepared using a non-toxic alcoholic vehicle. Suspensions can be formulated by dispersion of the compound in a non-toxic vehicle. Solubilisers and emulsifiers, such as, for example, ethoxylated isostearyl alcohols and polyoxyethylene sorbitol ethers, preservatives, flavour additives, such as, for example, peppermint oil or natural sweeteners or saccharin, or other artificial sweeteners and the like, can likewise be added.

The dosage unit formulations for oral administration can, if desired, be en-capsulated in microcapsules. The formulation can also be prepared in such a way that the release is extended or retarded, such as, for example, by coating or embedding of particulate material in polymers, wax and the like.

The compounds of the formula Ia or Ib and pharmaceutically acceptable salts, tautomers and stereoisomers thereof can also be administered in the form of liposome delivery systems, such as, for example, small unilamellar vesicles, large unilamellar vesicles and multilamellar vesicles. Liposomes can be formed from various phospholipids, such as, for example, cholesterol, stearylamine or phosphatidylcholines.

The compounds of the formula Ia or Ib and the pharmaceutically acceptable salts, tautomers and physiologically functional derivatives thereof can also be delivered using monoclonal antibodies as individual carriers to which the compound molecules are coupled. The compounds can also be coupled to soluble polymers as targeted medicament carriers. Such polymers may encompass polyvinylpyrrolidone, pyran copolymer, polyhydroxypropylmethacrylamidophenol, polyhydroxyethylaspartamidophenol or polyethylene oxide polylysine, substituted by palmitoyl radicals. The compounds may furthermore be coupled to a class of biodegradable polymers which are suitable for achieving controlled release of a medicament, for example polylactic acid, poly-epsilon-caprolactone, polyhydroxybutyric acid, polyorthoesters, poly-acetals, polydihydroxypyrans, polycyanoacrylates and crosslinked or amphipathic block copolymers of hydrogels.

Pharmaceutical formulations adapted for transdermal administration can be administered as independent plasters for extended, close contact with the epidermis of the recipient. Thus, for example, the active ingredient can be delivered from the plaster by iontophoresis, as described in general terms in Pharmaceutical Research, 3(6), 318 (1986).

Pharmaceutical compounds adapted for topical administration can be formulated as ointments, creams, suspensions, lotions, powders, solutions, pastes, gels, sprays, aerosols or oils.

For the treatment of the eye or other external tissue, for example mouth and skin, the formulations are preferably applied as topical ointment or cream. In the case of formulation to give an ointment, the active ingredient can be employed either with a paraffinic or a water-miscible cream base. Alternatively, the active ingredient can be formulated to give a cream with an oil-in-water cream base or a water-in-oil base.

Pharmaceutical formulations adapted for topical application to the eye include eye drops, in which the active ingredient is dissolved or suspended in a suitable carrier, in particular an aqueous solvent.

Pharmaceutical formulations adapted for topical application in the mouth encompass lozenges, pastilles and mouthwashes.

Pharmaceutical formulations adapted for rectal administration can be administered in the form of suppositories or enemas.

Pharmaceutical formulations adapted for nasal administration in which the carrier substance is a solid comprise a coarse powder having a particle size, for example, in the range 20-500 microns, which is administered in the manner in which snuff is taken, i.e. by rapid inhalation via the nasal passages from a container containing the powder held close to the nose. Suitable formulations for administration as nasal spray or nose drops with a liquid as carrier substance encompass active-ingredient solutions in water or oil.

Pharmaceutical formulations adapted for administration by inhalation encompass finely particulate dusts or mists, which can be generated by various types of pressurised dispensers with aerosols, nebulisers or insufflators.

Pharmaceutical formulations adapted for vaginal administration can be administered as pessaries, tampons, creams, gels, pastes, foams or spray formulations.

Pharmaceutical formulations adapted for parenteral administration include aqueous and non-aqueous sterile injection solutions comprising antioxidants, buffers, bacteriostatics and solutes, by means of which the formulation is rendered isotonic with the blood of the recipient to be treated; and aqueous and non-aqueous sterile suspensions, which may comprise suspension media and thickeners. The formulations can be administered in single-dose or multi-dose containers, for example sealed ampoules and vials, and stored in freeze-dried (lyophilised) state, so that only the addition of the sterile carrier liquid, for example water for injection purposes, immediately before use is necessary. Injection solutions and suspensions prepared in accordance with the recipe can be prepared from sterile powders, granules and tablets.

It goes without saying that, in addition to the above particularly mentioned constituents, the formulations may also comprise other agents usual in the art with respect to the particular type of formulation; thus, for example, formulations which are suitable for oral administration may comprise flavours.

A therapeutically effective amount of a compound of the formula Ia or Ib depends on a number of factors, including, for example, the age and weight of the animal, the precise condition that requires treatment, and its severity, the nature of the formulation and the method of administration, and is ultimately determined by the treating doctor or vet. However, an effective amount of a compound according to the invention is generally in the range from 0.1 to 100 mg/kg of body weight of the recipient (mammal) per day and particularly typically in the range from 1 to 10 mg/kg of body weight per day. Thus, the actual amount per day for an adult mammal weighing 70 kg is usually between 70 and 700 mg, where this amount can be administered as a single dose per day or usually in a series of part-doses (such as, for example, two, three, four, five or six) per day, so that the total daily dose is the same. An effective amount of a salt or solvate or of a physiologically functional derivative thereof can be determined as the fraction of the effective amount of the compound according to the invention per se. It can be assumed that similar doses are suitable for the treatment of other conditions mentioned above.

A combined treatment of this type can be achieved with the aid of simultaneous, consecutive or separate dispensing of the individual components of the treatment. Combination products of this type employ the compounds according to the invention.

The invention furthermore relates to medicaments comprising at least one compound of the formula Ia or Ib and/or pharmaceutically acceptable salts, tauotmers and stereoisomers thereof, including mixtures thereof in all ratios, and at least one further medicament active ingredient.

The invention also relates to a set (kit) consisting of separate packs of (a) an effective amount of a compound of the formula Ia or Ib and/or pharmaceutically acceptable salts, tautomers and stereoisomers thereof, including mixtures thereof in all ratios, and (b) an effective amount of a further medicament active ingredient.

The set comprises suitable containers, such as boxes, individual bottles, bags or ampoules. The set may, for example, comprise separate ampoules, each containing an effective amount of a compound of the formula Ia or Ib and/or pharmaceutically acceptable salts, solvates and stereoisomers thereof, including mixtures thereof in all ratios, and an effective amount of a further medicament active ingredient in dissolved or lyophilised form.

"Treating" as used herein, means an alleviation, in whole or in part, of symptoms associated with a disorder or disease, or slowing, or halting of further progression or worsening of those symptoms, or prevention or prophylaxis of the disease or disorder in a subject at risk for developing the disease or disorder.

The term "effective amount" in connection with a compound of formula Ia or Ib can mean an amount capable of alleviating, in whole or in part, symptoms associated with a disorder or disease, or slowing or halting further progression or worsening of those symptoms, or preventing or providing prophylaxis for the disease or disorder in a subject having or at risk for developing a disease disclosed herein, such as inflammatory conditions, immunological conditions, cancer or metabolic conditions.

In one embodiment an effective amount of a compound of formula Ia or Ib is an amount that inhibits PDHK in a cell, such as, for example, in vitro or in vivo. In some embodiments, the effective amount of the compound of formula Ia or Ib inhibits PDHK in a cell by 10%, 20%, 30%, 40%, 50%, 60%, 70%, 80%, 90% or 99%, compared to the activity of PDHK in an untreated cell. The effective amount of the compound of formula Ia or Ib, for example in a pharmaceutical composition, may be at a level that will exercise the desired effect; for example, about 0.005 mg/kg of a subject's body weight to about 10 mg/kg of a subject's body weight in unit dosage for both oral and parenteral administration.

Use

The present invention specifically relates to compounds of the formula Ia or Ib and pharmaceutically acceptable salts, tautomers and stereoisomers thereof, including mixtures thereof in all ratios, for the use for the treatment of cancer, diabetes and heart ischemia.

Moreover, the present invention relates to compounds of the formula Ia or Ib and pharmaceutically acceptable salts, tautomers and stereoisomers thereof, including mixtures thereof in all ratios, for the use for the treatment of insulin resistance syndrome, metabolic syndrome, hyperglycemia, dyslipidemia, atherosclerosis, cardiac failure, cardiomyopathy, myocardial ischemia, hyperlactacidemia, mitochondrial disease, mitochondrial encephalomyopathy.

The present invention specifically relates to methods for treating or preventing cancer, diabetes and heart ischemia, comprising administering to a subject in need thereof an effective amount of a compound of formula Ia or Ib or a pharmaceutically acceptable salt, tautomer, stereoisomer or solvate thereof.

Also encompassed is the use of the compounds of the formula Ia or Ib and/or pharmaceutically acceptable salts, tautomers and stereoisomers thereof for the preparation of a medicament for the treatment or prevention of a PDHK-induced disease or a PDHK-induced condition in a mammal, in which to this method a therapeutically effective amount of a compound according to the invention is administered to a sick mammal in need of such treatment. The therapeutic amount varies according to the specific disease and can be determined by the person skilled in the art without undue effort.

The expression "PDHK-induced diseases or conditions" refers to pathological conditions that depend on the activity of PDHK. Diseases associated with PDHK activity include cancer, diabetes and heart ischemia.

The present invention specifically relates to compounds of the formula Ia or Ib and pharmaceutically acceptable salts, tautomers and stereoisomers thereof, including mixtures thereof in all ratios, for the use for the treatment of diseases in which the inhibition, regulation and/or modulation inhibition of PDHK plays a role.

The present invention specifically relates to compounds of the formula Ia or Ib and pharmaceutically acceptable salts, tautomers and stereoisomers thereof, including mixtures thereof in all ratios, for the use for the inhibition of PDHK.

Representative cancers that compounds of formula Ia or Ib are useful for treating or preventing include, but are not limited to, cancer of the head, neck, eye, mouth, throat, esophagus, bronchus, larynx, pharynx, chest, bone, lung, colon, rectum, stomach, prostate, urinary bladder, uterine, cervix, breast, ovaries, testicles or other reproductive organs, skin, thyroid, blood, lymph nodes, kidney, liver, pancreas, brain, central nervous system, solid tumors and blood-borne tumors.

Moreover, representative cancers that compounds of formula Ia or Ib are useful for treating or preventing include cancer of brain (gliomas), glioblastomas, leukemias, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone and thyroid.

Preferably, the present invention relates to a method wherein the disease is a cancer.

Particularly preferable, the present invention relates to a method wherein the disease is a cancer, wherein administration is simultaneous, sequential or in alternation with administration of at least one other active drug agent.

The disclosed compounds of the formula Ia or Ib can be administered in combination with other known therapeutic agents, including anticancer agents. As used here, the term "anticancer agent" relates to any agent which is administered to a patient with cancer for the purposes of treating the cancer.

The anti-cancer treatment defined above may be applied as a monotherapy or may involve, in addition to the herein disclosed compounds of formula Ia or Ib, conventional surgery or radiotherapy or medicinal therapy. Such medicinal therapy, e.g. a chemotherapy or a targeted therapy, may include one or more, but preferably one, of the following anti-tumor agents:

Alkylating Agents such as altretamine, bendamustine, busulfan, carmustine, chlorambucil, chlormethine, cyclophosphamide, dacarbazine, ifosfamide, improsulfan, tosilate, lomustine, melphalan, mitobronitol, mitolactol, nimustine, ranimustine, temozolomide, thiotepa, treosulfan, mechloretamine, carboquone; apaziquone, fotemustine, glufosfamide, palifosfamide, pipobroman, trofosfamide, uramustine, TH-302[4], VAL-083[4];

Platinum Compounds such as carboplatin, cisplatin, eptaplatin, miriplatine hydrate, oxaliplatin, lobaplatin, nedaplatin, picoplatin, satraplatin;

lobaplatin, nedaplatin, picoplatin, satraplatin;

DNA Altering Agents such as amrubicin, bisantrene, decitabine, mitoxantrone, procarbazine, trabectedin, clofarabine;

amsacrine, brostallicin, pixantrone, laromustine[1,3];

Topoisomerase Inhibitors such as etoposide, irinotecan, razoxane, sobuzoxane, teniposide, topotecan; amonafide, belotecan, elliptinium acetate, voreloxin;

Microtubule Modifiers such as cabazitaxel, docetaxel, eribulin, ixabepilone, paclitaxel, vinblastine, vincristine, vinorelbine, vindesine, vinflunine;

fosbretabulin, tesetaxel;

Antimetabolites such as asparaginase[3], azacitidine, calcium levofolinate, capecitabine, cladribine, cytarabine, enocitabine, floxuridine, fludarabine, fluorouracil, gemcitabine, mercaptopurine, methotrexate, nelarabine, pemetrexed, pralatrexate, azathioprine, thioguanine, carmofur;

doxifluridine, elacytarabine, raltitrexed, sapacitabine, tegafur[2,3], trimetrexate;

Anticancer Antibiotics such as bleomycin, dactinomycin, doxorubicin, epirubicin, idarubicin, levamisole, miltefosine, mitomycin C, romidepsin, streptozocin, valrubicin, zinostatin, zorubicin, daunurobicin, plicamycin;

aclarubicin, peplomycin, pirarubicin;

Hormones/Antagonists such as abarelix, abiraterone, bicalutamide, buserelin, calusterone, chlorotrianisene, degarelix, dexamethasone, estradiol, fluocortolone fluoxymesterone, flutamide, fulvestrant, goserelin, histrelin, leuprorelin, megestrol, mitotane, nafarelin, nandrolone, nilutamide, octreotide, prednisolone, raloxifene, tamoxifen, thyrotropin alfa, toremifene, trilostane, triptorelin, diethylstilbestrol;

acolbifene, danazol, deslorelin, epitiostanol, orteronel, enzalutamide[1,3];

Aromatase Inhibitors such as aminoglutethimide, anastrozole, exemestane, fadrozole, letrozole, testolactone;

formestane;

Small Molecule Kinase Inhibitors such as crizotinib, dasatinib, erlotinib, imatinib, lapatinib, nilotinib, pazopanib, regorafenib, ruxolitinib, sorafenib, sunitinib, vandetanib, vemurafenib, bosutinib, gefitinib, axitinib;

afatinib, alisertib, dabrafenib, dacomitinib, dinaciclib, dovitinib, enzastaurin, nintedanib, lenvatinib, linifanib, linsitinib, masitinib, midostaurin, motesanib, neratinib, orantinib, perifosine, ponatinib, radotinib, rigosertib, tipifarnib, tivantinib, tivozanib, trametinib, pimasertib, brivanib alaninate, cediranib, apatinib[4], cabozantinib S-malate[1,3], ibrutinib[1,3], icotinib[4], buparlisib[2], cipatinib[4], cobimetinib[1,3], idelalisib[1,3], fedratinib[1], XL-647[4];

Photosensitizers such as methoxsalen[3];

porfimer sodium, talaporfin, temoporfin;

Antibodies such as alemtuzumab, besilesomab, brentuximab vedotin, cetuximab, denosumab, ipilimumab, ofatumumab, panitumumab, rituximab, tositumomab, trastuzumab, bevacizumab, pertuzumab[2,3];

catumaxomab, elotuzumab, epratuzumab, farletuzumab, mogamulizumab, necitumumab, nimotuzumab, obinutuzumab, ocaratuzumab, oregovomab, ramucirumab, rilotumumab, siltuximab, tocilizumab, zalutumumab, zanolimumab, matuzumab, dalotuzumab[1,2,3], onartuzumab[1,3], racotumomab[1], tabalumab[1,3], EMD-525797[4], nivolumab[1,3];

Cytokines such as aldesleukin, interferon alfa[2], interferon alfa2a[3], interferon alfa2b[2,3]; celmoleukin, tasonermin, teceleukin, oprelvekin[1,3], recombinant interferon beta-1a[4];

Drug Conjugates such as denileukin diftitox, ibritumomab tiuxetan, iobenguane I123, prednimustine, trastuzumab emtansine, estramustine, gemtuzumab, ozogamicin, aflibercept;

cintredekin besudotox, edotreotide, inotuzumab ozogamicin, naptumomab estafenatox, oportuzumab monatox, technetium (99mTc) arcitumomab[1,3], vintafolide[1,3];

Vaccines such as sipuleucel[3]; vitespen[3], emepepimut-S[3], oncoVAX[4], rindopepimut[3], troVax[4], MGN-1601[4], MGN-1703[4];

Miscellaneous alitretinoin, bexarotene, bortezomib, everolimus, ibandronic acid, imiquimod, lenalidomide, lentinan, metirosine, mifamurtide, pamidronic acid, pegaspargase, pentostatin, sipuleucel[3], sizofiran, tamibarotene, temsirolimus, thalidomide, tretinoin, vismodegib, zoledronic acid, vorinostat;

celecoxib, cilengitide, entinostat, etanidazole, ganetespib, idronoxil, iniparib, ixazomib, lonidamine, nimorazole, panobinostat, peretinoin, plitidepsin, pomalidomide, procodazol, ridaforolimus, tasquinimod, telotristat, thymalfasin, tirapazamine, tosedostat, trabedersen, ubenimex, valspodar, gendicine[4], picibanil[4], reolysin[4], retaspimycin hydrochloride[1,3], trebananib[2,3], virulizin[4], carfilzomib[1,3], endostatin[4], immucothel[4], belinostat[3], MGN-1703[4];

[1]Prop. INN (Proposed International Nonproprietary Name)
[2]Rec. INN (Recommended International Nonproprietary Names)
[3]USAN (United States Adopted Name)
[4]no INN.

The following abbreviations refer respectively to the definitions below:

aq (aqueous), h (hour), g (gram), L (liter), mg (milligram), MHz (Megahertz), min. (minute), mm (millimeter), mmol (millimole), mM (millimolar), m.p. (melting point), eq (equivalent), mL (milliliter), L (microliter), ACN (acetonitrile), AcOH (acetic acid), $CDCl_3$ (deuterated chloroform), $CD_3OD$ (deuterated methanol), $CH_3CN$ (acetonitrile), c-hex (cyclohexane), DCC (dicyclohexyl carbodiimide), DCM (dichloromethane), DIC (diisopropyl carbodiimide), DIEA (diisopropylethyl-amine), DMF (dimethylformamide), DMSO (dimethylsulfoxide), DMSO-$d_6$ (deuterated dimethylsulfoxide), EDC (1-(3-dimethyl-amino-propyl)-3-ethylcarbodiimide), ESI (Electro-spray ionization), EtOAc (ethyl acetate), $Et_2O$ (diethyl ether), EtOH (ethanol), HATU (dimethylamino-([1,2,3]triazolo[4,5-b]pyridin-3-yloxy)-methylene]-dimethyl-ammonium hexafluorophosphate), HPLC (High Performance Liquid Chromatography), i-PrOH (2-propanol), $K_2CO_3$ (potassium carbonate), LC (Liquid Chromatography), MeOH (methanol), $MgSO_4$ (magnesium sulfate), MS (mass spectrometry), MTBE (Methyl tert-butyl ether), $NaHCO_3$ (sodium bicarbonate), $NaBH_4$ (sodium borohydride), NMM (N-methyl morpholine), NMR (Nuclear Magnetic Resonance), PyBOP (benzotriazole-1-yloxy-tris-pyrrolidino-phosphonium hexafluorophosphate), RT (room temperature), Rt (retention time), SPE (solid phase extraction), TBTU (2-(1-H-benzotriazole-1-yl)-1,1,3,3-tetramethyluromium tetrafluoro borate), TEA (triethylamine), TFA (trifluoroacetic acid), THF (tetrahydrofuran), TLC (Thin Layer Chromatography), UV (Ultraviolet).

Description of the In Vitro Assays

Abbreviations

GST=Glutathione-S-transferase
FRET=Fluorescence resonance energy transfer
HTRF®=(homogenous time resolved fluorescence)
HEPES=4-(2-hydroxyethyl)-1-piperazine ethanesulfonic acid buffer
DTT=Dithiothreitol
BSA=bovine serum albumin
CHAPS=3-[(3-cholamidopropyl)dimethylammonio]-1-propanesulfonate Biochemical Activity Testing of PDHK2: PDC Inactivation Assay The biochemical activity assay for PDHK2 is based on the inactivation of PDC through phosphorylation by PDHK2. The assay is run in two steps: the enzymatic PDHK2 reaction in which isolated PDC is phosphorylated by PDHK2 with ATP as co-substrate and the PDC activity assay in which pyruvate and NAD are converted to acetyl-CoA and NADH. The PDC activity correlates to the increase in NADH and thereby is detectable directly via the increasing fluorescence signal (Exc 340 nm, Em 450 nm). Inhibition of PDHK2 results in a lower phosphorylation status and thereby a less decrease in activity of PDC and a stronger increase in NADH fluorescence signal.

The PDC inactivation assay is performed in Greiner 384-well microtiter plates and is used for high throughput screen. 4 μl of PDHK2 (human, rec, Carna Bioscience, 10 ng/μl-137 nM final concentration) and PDC (isolated from porcine heart, Sigma-Aldrich, 20 mU/ml final concentration) are incubated in the absence or presence of the test compound (10 dilution concentrations) for 30 min at room temperature in kinase buffer (15 mM potassium phosphate buffer, pH 7.0, 60 mM KCl, 1.5 mM DTT, 2.5 mM $MgCl_2$, 0.0125% (w/v) BSA, 0.125% Pluronic F-68). The kinase reaction is started by the addition of 4 μl ATP substrate solution (fc 5 μM in kinase buffer). After 30 min incubation at 37° C. 40 μl of PDC reaction solution (100 mM Tris/HCl, pH 7.8, 0.5 mM EDTA, 1 mM $MgCl_2$, 50 mM NaF, 0.25 mM Coenzyme A, 5 mM pyruvate, 1 mM NAD, 5 mM DTT, 1 mM thiamine pyrophosphate) is added. The first fluorescence measurement is performed on a Perkin Elmer Envision (Exc 340 nm, Em 450 nm). The reaction is incubated for 45 min at room temperature. Afterwards a second fluorescence measurement is performed and the PDC activity is calculated by the difference between both measurements. As full value for the PDHK2 assay the inhibitor-free PDHK2 reaction is used. The pharmacological zero value used is DCA (Sigma-Aldrich) in a final concentration of 3 mM. The inhibitory values (1050) were determined using either the program Symyx Assay Explorer® or Condosseo® from GeneData.

Isothermal Titration Calorimetry

ITC measurements were performed with a VP-ITC micro calorimeter (Microcal, LLC/GE Healthcare Bio-Sciences Aft Uppsala, Sweden). In general titrations were performed by titrating the protein (50 μM) to the test compound (5 μM) in 12 μl injections. All binding experiments were carried out at 30° C. In general the test compounds were diluted form DMSO stock solutions into the measurement buffer with a maximum final concentration of 1% DMSO. The measurement buffer was 20 mM HEPES, 135 mM KCl, 1 mM TCEP, 2 mM $MgCl_2$, 15 mM $NaH_2PO_4$, pH 7.5. The human PDHK2 (12-407) was produced in E. coli as his-tagged protein and purified by affinity chromatography. The tag was removed by side specific proteolysis. Before titration the protein buffer was changed to the measurement buffer containing the same DMSO concentration as the test compound dilution. ITC data analysis was performed using Origin 7 calorimetry software from the same supplier. For most measurements a binding model of one binding site was assumed. According to the applied mathematical model it is possible to calculate the binding constant ($K_A$), the observed binding enthalpy ($\Delta H^{obs}$) as well as the stoichiometry (N) of the formed complex. Preceding analysis the raw data was corrected for the heats of dilution by extrapolating from the saturation value from the end of titration. In order to allow for direct comparison between the respective experimental series and protein preparations the protein concentration was corrected by referencing titrations to a well behaved standard inhibitor. The apparent stoichiometry values defined the fraction of binding competent protein and compensated for relative errors in protein concentration measurements. This corrected protein concentration was used to set up ITC experiment series with test compounds. Any deviations from ideal 1:1 stoichiometry observed here were attributed to errors in compound concentration. This nominal compound concentration was corrected as well to achieve 1:1 stoichiometry in the fit.

Cellular Assay for Determination of Compound Activities

Compound activities were determined in a cellular immunofluorescence assay. Human HEK293T cells were seeded into black 384-well plates with clear bottom and grown overnight.

Next day, test compounds were added to the wells and the plates incubated for 5 hours. Following this, cells were fixed with formaldehyde, permeabilised and blocked. The primary antibody, Anti-PDH-E1 alpha (pSer300), AP1064 (Merck Millipore) was added and incubated overnight in the plate wells. Next, cells were washed and the seconday antibody, Alexa Fluor 488, goat anti-rabbit ab (A-11008, Invitrogen) was added together with Hoechst 33258 (H3569, Invitrogen) and incubated for 1 hour in the plate wells. Finally, cells were washed and the plates were measured on the laser scanning cytometer acumen hci (TTpLabtech).

The raw data were normalized against a pharmacological inhibitor control and dose response curves were generated by plotting the percent effect values using the software package Genedata screener (Genedata).

Above and below, all temperatures are indicated in ° C. In the following examples, "conventional work-up" means: water is added if necessary, the pH is adjusted, if necessary, to values between 2 and 10, depending on the constitution of the end product, the mixture is extracted with ethyl acetate or dichloromethane, the phases are separated, the organic phase is dried over sodium sulfate and evaporated, and the residue is purified by chromatography on silica gel and/or by crystallisation.

LC/MS:
HPLC-Method:
Gradient: 3.3 min; Flow: 2.4 ml/min from 0 min 4% B, 2.8 min 100% B, 3.3 min 100% B
A: Water+HCOOH (0.05% Vol.); B: Acetonitril+HCOOH (0.04% Vol.)
Column: Chromolith SpeedROD RP 18e 50-4.6
Wave Length: 220 nm
Agilent Apparatus $^1$H NMR was recorded on Bruker DPX-300, DRX-400, AVII-400 or BRUKER 500 MHz spectrometer, using residual signal of deuterated solvent as internal reference. Chemical shifts (δ) are reported in ppm relative to the residual solvent signal (δ=2.49 ppm for $^1$H NMR in DMSO-$d_6$). $^1$H NMR data are reported as follows: chemical shift (multiplicity, coupling constants, and number of hydrogens). Multiplicity is abbreviated as follows: s (singlet), d (doublet), t (triplet), q (quartet), m (multiplet), br (broad).

EXAMPLES

General reaction scheme for manufacturing compounds of formula Ia in which X=N and Y=CH

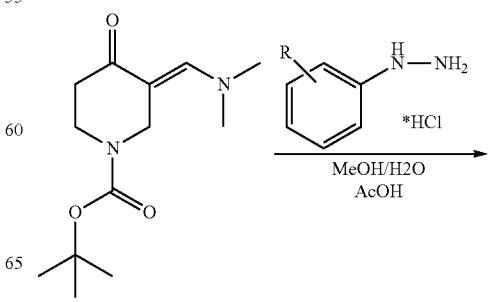

-continued

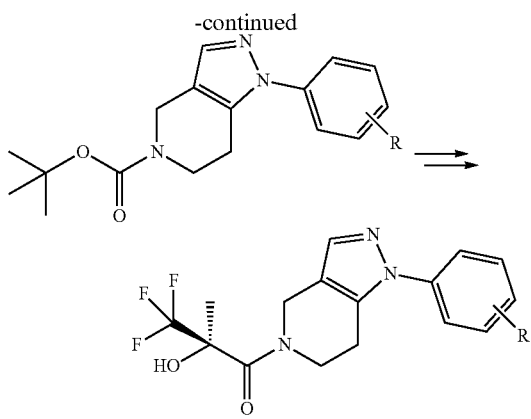

Example 1

(2R)-1-[1-(4-chlorophenyl)-6,7-dihydro-4H-pyrazolo[4,3-c]pyridin-5-yl]-3,3,3-trifluoro-2-hydroxy-2-methyl-propan-1-one ("A1")

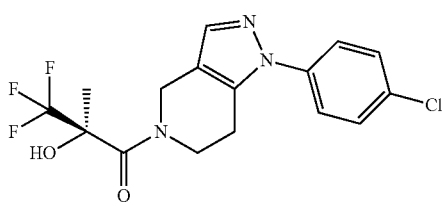 [SMILES: C[C@@](O)(C(=O)N1CCc2c(cnn2-c2ccc(Cl)cc2)C1)C(F)(F)F]

1.1 1-(4-Chloro-phenyl)-1,4,6,7-tetrahydro-pyrazolo[4,3-c]pyridine-5-carboxylic acid tert-butyl ester 3-[1-Dimethylamino-meth-(E)-ylidene]-4-oxo-piperidine-1-carboxylic acid tert-butyl ester (200 mg; 0.786 mmol) and 4-chlorophenylhydrazine hydrochloride (155 mg; 0.865 mmol) were suspended in methanol (4 mL) and water (1 mL). Glacial acetic acid (0.23 mL; 3.932 mmol) was added while stirring and a few minutes later an orange solution was formed. The mixture was stirred for 1 h at room temperature, diluted with ethyl acetate, washed with water, saturated NaHCO₃ solution and brine, dried with Na₂SO₄, filtered and evaporated to dryness. The oily residue was purified by flash chromatography (Companion RF; 40 g Si50 silica gel column). Yield: 145.5 mg brown oil; LC/MS, Rt: 2.61 min; (M+H) 334.1

1.2 1-(4-Chloro-phenyl)-4,5,6,7-tetrahydro-1H-pyrazolo[4,3-c]pyridine dihydrochloride Compound 1.1 (145.5 mg; 0.436 mmol) was dissolved in dry 1,4-dioxane (3 mL) and hydrogen chloride (4 M solution in dioxane; 4 mL) was added at room temperature. After a few minutes a light brown solid precipitated. The reaction mixture was stirred for 2 h at room temperature, diluted with diethylether (7 mL) and stirred for 5 min. The precipitate was filtered by suction, washed with diethylether and dried for 2 h at room temperature. Yield: 155 mg yellow solid; LC/MS, Rt: 1.16 min; (M+H) 234.1

1.3 (2R)-1-[1-(4-chlorophenyl)-6,7-dihydro-4H-pyrazolo[4,3-c]pyridin-5-yl]-3,3,3-trifluoro-2-hydroxy-2-methyl-propan-1-one Compound 1.2 (155 mg; 0.505 mmol), (R)-3,3,3-trifluoro-2-hydroxy-2-methyl-propionic acid (159 mg; 1.006 mmol) and [dimethylamino-([1,2,3]triazolo[4,5-b]pyridin-3-yloxy)-methylene]-dimethyl-ammonium; hexafluoro phosphate (383 mg; 1.007 mmol) were dissolved in DMF (2.5 mL). N-Ethyldiisopropylamine (0.857 mL; 5.037 mmol) was added and the yellow solution was stirred overnight at room temperature. The reaction mixture was diluted with water (40 mL) and extracted ethyl acetate. The combined organic layers were washed with saturated NaHCO₃ solution, and brine, dried with Na₂SO₄, filtered and evaporated to dryness. The residue was purified by flash chromatography (Companion RF, 24 g Si50 silica gel column) and subsequently by preparative HPLC (Agilent 1260; column: Waters SunFire C18, 5 μm, 30×150 mm). The collected fractions with product were combined and evaporated to an aqueous residue. This aqueous residue was rendered basic with saturated NaHCO₃ solution and extracted with ethyl acetate. The combined organic layers were washed with brine, dried with Na₂SO₄, filtered, evaporated to dryness, and the residue was lyophilized.

Yield: 114 mg (60%) pale-yellow powder; LC/MS, Rt: 2.19 min; (M+H) 374.1;
$^1$H NMR (500 MHz, DMSO-d$_6$) δ 7.66-7.51 (m, 5H), 7.19 (s, 1H), 5.14-4.84 (m, 1H), 4.65-4.47 (m, 1H), 4.23-3.96 (m, 1H), 3.90-3.64 (m, 1H), 3.04-2.80 (m, 2H), 1.66-1.46 (m, 3H).

Example 2

(2R)-1-[2-(4-chlorophenyl)-6,7-dihydro-4H-pyrazolo[4,3-c]pyridin-5-yl]-3,3,3-trifluoro-2-hydroxy-2-methyl-propan-1-one ("A2")

"A2", which is the isomeric cyclisation product of step 1.1, was isolated in step 1.3 by preparative HPLC (Agilent 1260; column: Waters SunFire C18, 5 μm, 30×150 mm). Yield: 7 mg (4%) colorless powder; LC/MS, Rt: 2.26 min; (M+H) 374.1; $^1$H NMR (500 MHz, DMSO-d$_6$) δ 8.33 (s, 1H), 7.82-7.76 (m, 2H), 7.55-7.50 (m, 2H), 7.21 (s, 1H), 5.16-4.94 (m, 1H), 4.69-4.50 (m, 1H), 4.28-4.02 (m, 1H), 3.94-3.68 (m, 1H), 2.93-2.68 (m, 2H), 1.66-1.45 (m, 3H).

Example 3

(R)-3,3,3-Trifluoro-2-hydroxy-2-methyl-1-(1-phenyl-1,4,6,7-tetrahydro-pyrazolo[4,3-c]pyridin-5-yl)-propan-1-one ("A3")

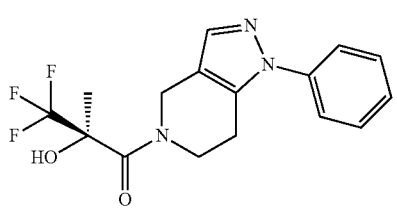 [SMILES: C[C@@](O)(C(=O)N1CCc2c(cnn2-c2ccccc2)C1)C(F)(F)F]

Preparation as described for example 1 (steps 1.1-1.3). Yield: 142 mg (62%) colorless solid; LC/MS, Rt: 1.97 min; (M+H) 340.1; $^1$H NMR (400 MHz, DMSO-d$_6$) δ 7.58-7.52

(m, 3H), 7.52-7.45 (m, 2H), 7.38-7.31 (m, 1H), 6.87 (s, 1H), 4.73 (s, 2H), 4.09-3.90 (m, 2H), 2.91 (t, J=5.8 Hz, 2H), 1.58 (s, 3H).

Example 4

(R)-3,3,3-Trifluoro-1-[1-(4-fluoro-phenyl)-1,4,6,7-tetrahydro-pyrazolo[4,3-c]pyridin-5-yl]-2-hydroxy-2-methyl-propan-1-one ("A4")

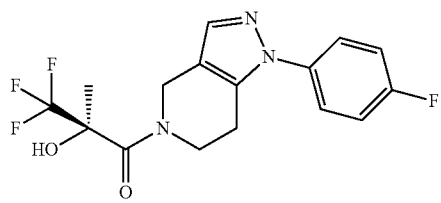 [SMILES: C[C@@](O)(C(=O)N1CCc2c(cnn2-c2ccc(F)cc2)C1)C(F)(F)F]

Preparation as described for example 1 (steps 1.1-1.3). Yield: 102 mg (77%) colorless solid; LC/MS, Rt: 2.02 min; (M+H) 358.2; $^1$H NMR (400 MHz, DMSO-$d_6$) δ 7.63-7.54 (m, 3H), 7.35-7.27 (m, 2H), 6.90 (s, 1H), 4.81-4.67 (m, 2H), 4.09-3.93 (m, 2H), 2.90 (t, J=5.8 Hz, 2H), 1.60 (s, 3H).

Example 5

(R)-1-[1-(2,4-Difluoro-phenyl)-1,4,6,7-tetrahydro-pyrazolo[4,3-c]pyridin-5-yl]-3,3,3-trifluoro-2-hydroxy-2-methyl-propan-1-one ("A5")

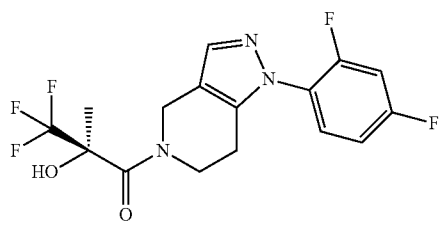 [SMILES: C[C@@](O)(C(=O)N1CCc2c(cnn2-c2ccc(F)cc2F)C1)C(F)(F)F]

Preparation as described for example 1 (steps 1.1-1.3). Yield: 160 mg (77%) pale-yellow solid; LC/MS, Rt: 1.99 min; (M+H) 376.1; $^1$H NMR (400 MHz, DMSO-$d_6$) δ 7.68-7.50 (m, 3H), 7.26 (t, J=7.9 Hz, 1H), 7.23-7.10 (m, 1H), 5.18-3.62 (m, 4H), 2.81-2.54 (m, 2H), 1.56 (s, 3H).

Example 6

(R)-1-[2-(2,4-Difluoro-phenyl)-2,4,6,7-tetrahydropyrazolo[4,3-c]pyridin-5-yl]-3,3,3-trifluoro-2-hydroxy-2-methyl-propan-1-one ("A6")

The isomeric cyclisation product of step 5.1 was isolated by flash chromatography (Companion RF; 24 g Si50 silica gel column) and converted to example 6 as described for example 1 (steps 1.2-1.3). Yield: 51 mg (79%) colorless solid; LC/MS, Rt: 2.09 min; (M+H) 376.1; $^1$H NMR (400 MHz, DMSO-$d_6$, 80° C.) δ 7.95 (d, J=2.4 Hz, 1H), 7.81-7.74 (m, 1H), 7.46-7.39 (m, 1H), 7.23-7.16 (m, 1H), 6.95 (s, 1H), 4.88-4.73 (m, 2H), 4.15-3.95 (m, 2H), 2.82 (t, J=5.9 Hz, 2H), 1.59 (s, 3H).

Example 7

(R)-1-(1-tert-Butyl-1,4,6,7-tetrahydro-pyrazolo[4,3-c]pyridin-5-yl)-3,3,3-trifluoro-2-hydroxy-2-methyl-propan-1-one ("A7")

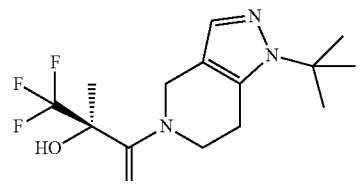

Preparation as described for example 1 (steps 1.1-1.3). Yield: 131 mg (57%) yellow solid; LC/MS, Rt: 1.85 min; (M+H) 320.2; $^1$H NMR (500 MHz, DMSO-$d_6$) δ 7.23 (s, 1H), 7.15 (s, 1H), 5.07-3.61 (m, 4H), 3.07-2.80 (m, 2H), 1.52 (s, 12H).

Example 8

(R)-1-(2-tert-Butyl-2,4,6,7-tetrahydro-pyrazolo[4,3-c]pyridin-5-yl)-3,3,3-trifluoro-2-hydroxy-2-methyl-propan-1-one ("A8")

The isomeric cyclisation product of step 7.1 was isolated by preparative HPLC (Agilent 1260; column: Waters SunFire C18, 5 μm, 30×150 mm) and converted to example 8 as described for example 1 (steps 1.2-1.3). Yield: 16 mg (26%) colorless solid; LC/MS, Rt: 1.85 min; (M+H) 320.1.

General reaction scheme for manufacturing compounds of formula Ia in which X=N, Y=CH and $R^2$ denotes $CH_3$

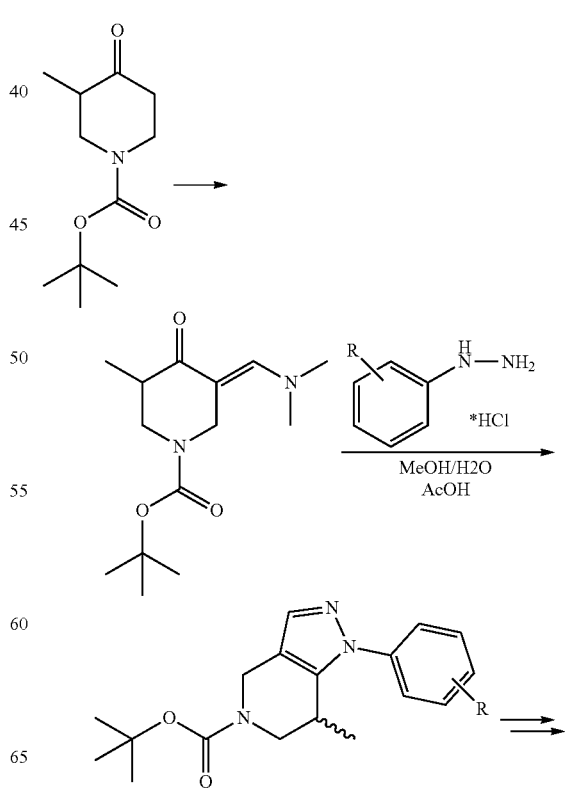

-continued

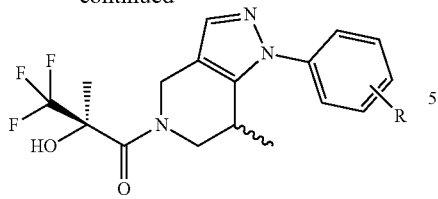

Example 9

(2R)-1-[1-(4-chlorophenyl)-7-methyl-6,7-dihydro-4H-pyrazolo[4,3-c]pyridin-5-yl]-3,3,3-trifluoro-2-hydroxy-2-methyl-propan-1-one ("A9"); Mixture of Diastereomers

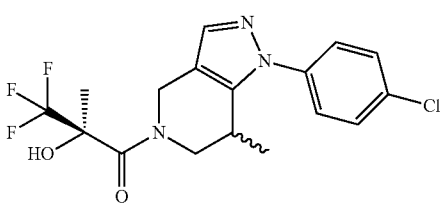 [SMILES: CC1CN(C(=O)[C@@](C)(O)C(F)(F)F)Cc2cnn(-c3ccc(Cl)cc3)c21]

9.1 3-[1-Dimethylamino-meth-(E)-ylidene]-5-methyl-4-oxo-piperidine-1-carboxylic acid tert-butyl ester N-Boc-3-methyl-4-piperidone (1.00 g; 4.689 mmol) was dissolved in tert-butoxy bis(dimethylamino)methane (1.14 g; 6.564 mmol). The reaction vial was sealed with a septum and stirred for 30 min at 100° C. The reaction mixture was cooled to room temperature, diluted with water (20 mL) and extracted with ethyl acetate. The combined organic layers were washed with brine, dried with $Na_2SO_4$, filtered by suction and evaporated to dryness. The yellow oil (1.24 g) was used in the next step without further purification. Steps 9.2-9.4 were performed as described for example 1 (steps 1.1-1.3). Yield: 179 mg (74%) colorless solid; LC/MS, Rt: 2.22 min; (M+H) 388.1; $^1$H NMR (400 MHz, DMSO-$d_6$, 90° C.) δ 7.62-7.52 (m, 5H), 6.91 (d, J=3.2 Hz, 1H), 5.11-4.76 (m, 1H), 4.69 (dd, J=15.8, 8.9 Hz, 1H), 3.95 (dd, J=13.1, 5.3 Hz, 1H), 3.92-3.76 (m, 1H), 3.42 (h, J=6.2 Hz, 1H), 1.63-1.57 (m, 3H), 0.89 (dd, J=6.8 Hz, 2.5 Hz, 3H).

Example 10

(R)-1-[(R)-1-(4-Chloro-phenyl)-7-methyl-1,4,6,7-tetrahydro-pyrazolo[4,3-c]pyridin-5-yl]-3,3,3-trifluoro-2-hydroxy-2-methyl-propan-1-one ("A10")

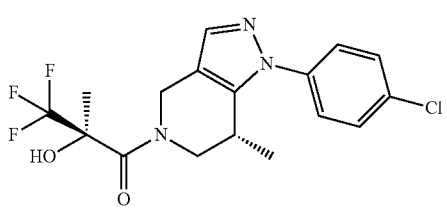 [SMILES: C[C@@H]1CN(C(=O)[C@@](C)(O)C(F)(F)F)Cc2cnn(-c3ccc(Cl)cc3)c21]

Example 11

(R)-1-[(S)-1-(4-Chloro-phenyl)-7-methyl-1,4,6,7-tetrahydro-pyrazolo[4,3-c]pyridin-5-yl]-3,3,3-trifluoro-2-hydroxy-2-methyl-propan-1-one ("A11")

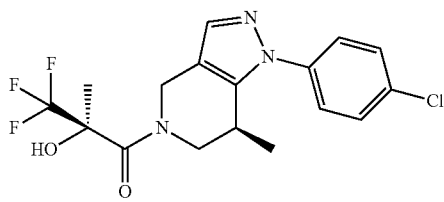 [SMILES: C[C@H]1CN(C(=O)[C@@](C)(O)C(F)(F)F)Cc2cnn(-c3ccc(Cl)cc3)c21]

The preparative separation of the diastereomers of example 9 was performed by SFC (column: ChiralCel OJ-H; eluent: $CO_2$:methanol-92:8). The combined fractions were evaporated to dryness. The oily residue was dissolved in acetonitrile, diluted with water and lyophilized.

"A10": 66 mg colorless solid; LC/MS, Rt: 2.22 min; (M+H) 388.1; $^1$H NMR (400 MHz, DMSO-$d_6$, 80° C.) δ 7.68-7.47 (m, 4H), 6.94 (s, 1H), 5.08-4.55 (m, 2H), 4.08-3.66 (m, 2H), 3.51-3.32 (m, 1H), 1.60 (s, 3H), 0.88 (d, J=6.8 Hz, 3H).

"A11": 68 mg yellow solid; LC/MS, Rt: 2.23 min; (M+H) 388.1; $^1$H NMR (400 MHz, DMSO-$d_6$, 80° C.) δ 7.65-7.48 (m, 4H), 6.94 (s, 1H), 5.20-4.59 (m, 2H), 4.08-3.66 (m, 2H), 3.52-3.30 (m, 1H), 1.58 (s, 3H), 0.87 (d, J=6.8 Hz, 3H).

Example 12

(2R)-3,3,3-trifluoro-1-[1-(4-fluorophenyl)-7-methyl-6,7-dihydro-4H-pyrazolo[4,3-c]pyridin-5-yl]-2-hydroxy-2-methyl-propan-1-one ("A12"); Mixture of Diastereomers

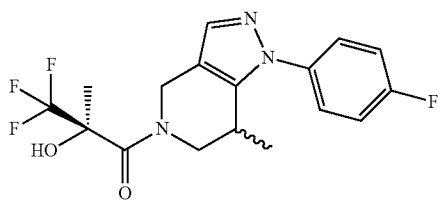 [SMILES: CC1CN(C(=O)[C@@](C)(O)C(F)(F)F)Cc2cnn(-c3ccc(F)cc3)c21]

Preparation as described for "A9" (steps 9.1-9.4). Yield: 185 mg (66%) colorless solid; LC/MS, Rt: 2.07 min; (M+H) 372.2; $^1$H NMR (400 MHz, DMSO-$d_6$, 80° C.) δ 7.60-7.49 (m, 3H), 7.37-7.27 (m, 2H), 6.96 (s, 1H), 5.17-4.77 (m, 1H), 4.68 (dd, J=15.7, 7.5 Hz, 1H), 3.98-3.75 (m, 2H), 3.36 (h, J=6.2 Hz, 1H), 1.58 (d, J=5.3 Hz, 3H), 0.84 (dd, J=6.8, 2.3 Hz, 3H).

Example 13

(2R)-3,3,3-trifluoro-1-[2-(4-fluorophenyl)-7-methyl-6,7-dihydro-4H-pyrazolo[4,3-c]pyridin-5-yl]-2-hydroxy-2-methyl-propan-1-one ("A13"); Mixture of Diastereomers The isomeric cyclisation product of step 12.1 was isolated by flash chromatography (Companion RF; 24 g Si50 silica gel column) and converted to example 13 as described for example 9 (steps 9.3-9.4). Yield: 29 mg (75%) colorless powder; LC/MS, Rt: 2.20/2.22 min; (M+H) 372.1; ¹H NMR (400 MHz, DMSO-$d_6$) δ 8.29-8.24 (m, 1H), 7.83-7.75 (m, 2H), 7.37-7.28 (m, 2H), 7.27-7.14 (m, 1H), 5.34-4.97 (m, 1H), 4.95-4.50 (m, 1H), 4.25-3.91 (m, 1H), 3.39-3.20 (m, 1H), 3.19-2.89 (m, 1H), 1.68-1.45 (m, 3H), 1.25 (d, J=5.8 Hz, 3H).

Example 14

(R)-3,3,3-Trifluoro-1-[(R)-1-(4-fluoro-phenyl)-7-methyl-1,4,6,7-tetrahydro-pyrazolo[4,3-c]pyridin-5-yl]-2-hydroxy-2-methyl-propan-1-one ("A14")

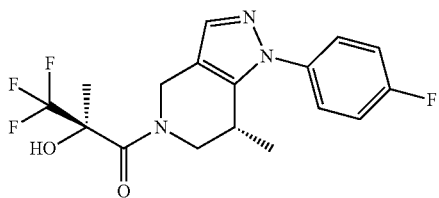 [SMILES: C[C@@H]1CN(C(=O)[C@@](C)(O)C(F)(F)F)Cc2cnn(-c3ccc(F)cc3)c21]

Example 15

(R)-3,3,3-Trifluoro-1-[(S)-1-(4-fluoro-phenyl)-7-methyl-1,4,6,7-tetrahydro-pyrazolo[4,3-c]pyridin-5-yl]-2-hydroxy-2-methyl-propan-1-one ("A15")

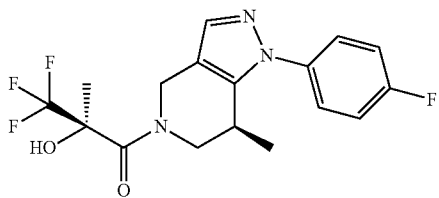 [SMILES: C[C@H]1CN(C(=O)[C@@](C)(O)C(F)(F)F)Cc2cnn(-c3ccc(F)cc3)c21]

The preparative separation of the diastereomers of example 12 was performed by SFC (column: ChiralCel OJ-H; eluent: $CO_2$:methanol-95:5). The combined fractions were evaporated to dryness. The oily residue was dissolved in acetonitrile, diluted with water and lyophilized.
"A14": 66 mg colorless solid; LC/MS, Rt: 2.07 min; (M+H) 372.1; ¹H NMR (400 MHz, DMSO-$d_6$, 80° C.) δ 7.64-7.52 (m, 2H), 7.51 (s, 1H), 7.38-7.22 (m, 2H), 6.92 (s, 1H), 5.18-4.50 (m, 2H), 4.00-3.58 (m, 2H), 3.50-3.20 (m, 1H), 1.58 (s, 3H), 0.84 (d, J=6.8 Hz, 3H).
"A15": 65 mg colorless solid; LC/MS, Rt: 2.08 min; (M+H) 372.1; ¹H NMR (400 MHz, DMSO-$d_6$, 80° C.) δ 7.64-7.53 (m, 2H), 7.51 (s, 1H), 7.39-7.23 (m, 2H), 6.91 (s, 1H), 5.16-4.56 (m, 2H), 4.19-3.58 (m, 2H), 3.44-3.27 (m, 1H), 1.57 (s, 3H), 0.83 (d, J=6.8 Hz, 3H).
Alternative method for the preparation of "A14" and "A15": Preparative separation of the enantiomers of the Boc-protected cyclization products (step 12.1) was accomplished by SFC (column: ChiralCel OJ-H; eluent: $CO_2$:2-propanol-95:5). Both enantiomers were converted to "A14" and "A15" respectively as described for "A9" (steps 9.3-9.4).

Example 16

(R)-3,3,3-Trifluoro-2-hydroxy-2-methyl-1-(7-methyl-1-phenyl-1,4,6,7-tetra-hydro-pyrazolo[4,3-c]pyridin-5-yl)-propan-1-one ("A16"); Mixture of Diastereomers

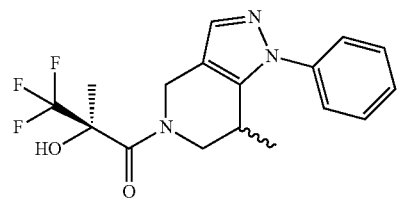 [SMILES: CC1CN(C(=O)[C@@](C)(O)C(F)(F)F)Cc2cnn(-c3ccccc3)c21]

Preparation as described for "A9" (steps 9.1-9.4). Yield: 176 mg (78%) colorless solid; LC/MS, Rt: 2.02 min; (M+H) 354.2; ¹H NMR (400 MHz, DMSO-$d_6$, 80° C.) δ 7.56-7.48 (m, 5H), 7.46-7.38 (m, 1H), 6.94 (s, 1H), 5.16-4.77 (m, 1H), 4.70 (dd, J=15.6, 6.6 Hz, 1H), 4.02-3.73 (m, 2H), 3.41 (h, J=6.3 Hz, 1H), 1.59 (d, J=5.0 Hz, 3H), 0.85 (dd, J=6.8, 2.7 Hz, 3H).

Example 17

(R)-3,3,3-Trifluoro-2-hydroxy-2-methyl-1-(7-methyl-2-phenyl-2,4,6,7-tetra-hydro-pyrazolo[4,3-c]pyridin-5-yl)-propan-1-one ("A17"); mixture of diastereomers The isomeric cyclisation product of step 16.1 was isolated by flash chromatography (Companion RF; 24 g Si50 silica gel column) and converted to example 17 as described for "A9" (steps 9.3-9.4). Yield: 41 mg (71%) pale-yellow solid; LC/MS, Rt: 2.16/2.18 min; (M+H) 354.2; ¹H NMR (400 MHz, DMSO-$d_6$) δ 8.33-8.25 (m, 1H), 7.79-7.73 (m, 2H), 7.52-7.44 (m, 2H), 7.31-7.25 (m, 1H), 7.25-7.12 (m, 1H), 5.36-4.99 (m, 1H), 4.97-4.53 (m, 1H), 4.27-3.88 (m, 1H), 3.41-2.92 (m, 2H), 1.69-1.44 (m, 3H), 1.31-1.19 (m, 3H).

Example 18

(R)-3,3,3-Trifluoro-2-hydroxy-2-methyl-1-((R)-7-methyl-1-phenyl-1,4,6,7-tetrahydro-pyrazolo[4,3-c]pyridin-5-yl)-propan-1-one ("A18")

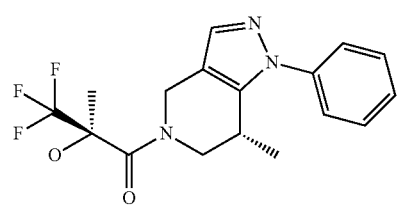 [SMILES: C[C@@H]1CN(C(=O)[C@@](C)(O)C(F)(F)F)Cc2cnn(-c3ccccc3)c21]

Example 19

(R)-3,3,3-Trifluoro-2-hydroxy-2-methyl-1-((S)-7-methyl-1-phenyl-1,4,6,7-tetrahydro-pyrazolo[4,3-c]pyridin-5-yl)-propan-1-one ("A19")

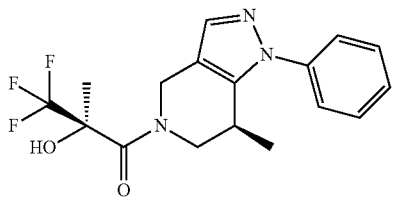 [SMILES: C[C@H]1CN(C(=O)[C@@](C)(O)C(F)(F)F)Cc2cnn(-c3ccccc3)c21]

The preparative separation of the diastereomers of "A16" was performed by SFC (column: ChiralCel OJ-H; eluent: $CO_2$:methanol-95:5). The combined fractions were evaporated to dryness. The oily residue was dissolved in acetonitrile, diluted with water and lyophilized.

"A18": 54 mg colorless solid; LC/MS, Rt: 2.02 min; (M+H) 354.2; $^1$H NMR (400 MHz, DMSO-$d_6$, 80° C.) δ 7.57-7.45 (m, 5H), 7.45-7.33 (m, 1H), 6.92 (s, 1H), 5.32-4.45 (m, 2H), 4.14-3.53 (m, 2H), 3.53-3.25 (m, 1H), 1.58 (d, 3H), 0.84 (d, J=6.8 Hz, 3H).

"A19": 63 mg colorless solid; LC/MS, Rt: 2.03 min; (M+H) 354.1; $^1$H NMR (400 MHz, DMSO-$d_6$, 80° C.) δ 7.57-7.46 (m, 5H), 7.45-7.34 (m, 1H), 6.91 (s, 1H), 5.23-4.51 (m, 2H), 4.10-3.59 (m, 2H), 3.50-3.31 (m, 1H), 1.57 (s, 3H), 0.83 (d, J=6.8 Hz, 3H).

Example 20

(R)-1-[(R)-1-(2,4-Difluoro-phenyl)-7-methyl-1,4,6,7-tetrahydro-pyrazolo[4,3-c]pyridin-5-yl]-3,3,3-trifluoro-2-hydroxy-2-methyl-propan-1-one ("A20")

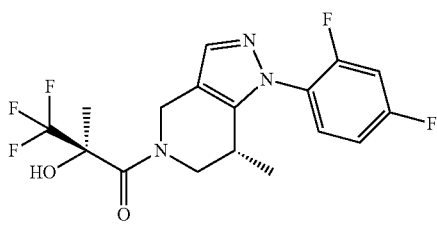 [SMILES: C[C@@H]1CN(C(=O)[C@@](C)(O)C(F)(F)F)Cc2cnn(-c3ccc(F)cc3F)c21]

Example 21

(R)-1-[(S)-1-(2,4-Difluoro-phenyl)-7-methyl-1,4,6,7-tetrahydro-pyrazolo[4,3-c]pyridin-5-yl]-3,3,3-trifluoro-2-hydroxy-2-methyl-propan-1-one ("A21")

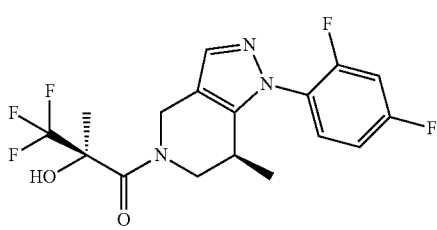 [SMILES: C[C@H]1CN(C(=O)[C@@](C)(O)C(F)(F)F)Cc2cnn(-c3ccc(F)cc3F)c21]

Preparation as described for "A9" (steps 9.1-9.4). The preparative separation of the diastereomers was performed by SFC (column: ChiralPak AS-H; eluent: $CO_2$:2-propanol-97:3). The combined fractions were evaporated to dryness. The oily residue was dissolved in acetonitrile, diluted with water and lyophilized.

"A20": 35 mg colorless solid; LC/MS, Rt: 2.09 min; (M+H) 390.1; $^1$H NMR (400 MHz, DMSO-$d_6$, 80° C.) δ 7.68-7.53 (m, 2H), 7.53-7.40 (m, 1H), 7.33-7.14 (m, 1H), 6.97 (s, 1H), 5.32-4.36 (m, 2H), 4.22-3.47 (m, 2H), 3.25-2.87 (m, 1H), 1.60 (s, 3H), 0.82 (d, J=6.9 Hz, 3H).

"A21": 35 mg colorless solid; LC/MS, Rt: 2.10 min; (M+H) 390.1; $^1$H NMR (400 MHz, DMSO-$d_6$, 80° C.) δ 7.67-7.54 (m, 2H), 7.53-7.40 (m, 1H), 7.27-7.18 (m, 1H), 6.96 (s, 1H), 5.08-4.49 (m, 2H), 4.21-3.44 (m, 2H), 3.19-2.96 (m, 1H), 1.58 (s, 3H), 0.81 (d, J=6.8 Hz, 3H).

Example 22

(R)-1-((R)-1-tert-Butyl-7-methyl-1,4,6,7-tetrahydro-pyrazolo[4,3-c]pyridin-5-yl)-3,3,3-trifluoro-2-hydroxy-2-methyl-propan-1-one ("A22")

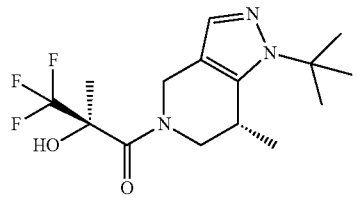 [SMILES: C[C@@H]1CN(C(=O)[C@@](C)(O)C(F)(F)F)Cc2cnn(C(C)(C)C)c21]

Example 23

(R)-1-((S)-1-tert-Butyl-7-methyl-1,4,6,7-tetrahydro-pyrazolo[4,3-c]pyridin-5-yl)-3,3,3-trifluoro-2-hydroxy-2-methyl-propan-1-one ("A23")

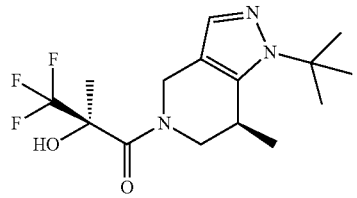 [SMILES: C[C@H]1CN(C(=O)[C@@](C)(O)C(F)(F)F)Cc2cnn(C(C)(C)C)c21]

Preparation as described for "A9" (steps 9.1-9.4). The preparative separation of the diastereomers was performed by SFC (column: ChiralPak AD-H; eluent: $CO_2$:2-methanol-92:8). The combined fractions were evaporated to dryness. The oily residue was dissolved in acetonitrile, diluted with water and lyophilized.

"A22": 52 mg colorless solid; LC/MS, Rt: 1.99 min; (M+H) 334.2; $^1$H NMR (400 MHz, DMSO-$d_6$, 80° C.) δ 7.20 (s, 1H), 6.87 (s, 1H), 5.24 (s, 1H), 4.65 (s, 1H), 4.18 (d, J=15.5 Hz, 1H), 3.51-3.25 (m, 1H), 3.11-2.93 (m, 1H), 1.59 (s, 3H), 1.56 (s, 9H), 1.19 (d, J=6.7 Hz, 3H).

"A23": 42 mg colorless solid; LC/MS, Rt: 1.85 min; (M+H) 334.2; $^1$H NMR (400 MHz, DMSO-$d_6$, 80° C.) δ 7.21 (s, 1H), 6.84 (s, 1H), 5.36-5.02 (m, 1H), 4.60 (d, J=12.8 Hz, 1H), 4.21 (d, J=16.0 Hz, 1H), 3.40-3.32 (m, 1H), 3.07-2.98 (m, 1H), 1.59-1.53 (m, 12H), 1.19 (d, J=6.7 Hz, 3H).

Example 24

(R)-3,3,3-Trifluoro-1-[(R)-1-(2-fluoro-phenyl)-7-methyl-1,4,6,7-tetrahydro-pyrazolo[4,3-c]pyridin-5-yl]-2-hydroxy-2-methyl-propan-1-one ("A24")

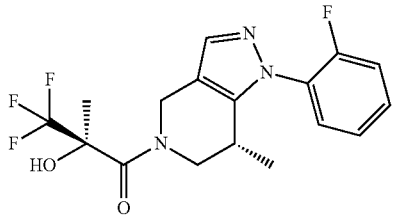 [SMILES: C[C@@H]1CN(C(=O)[C@@](C)(O)C(F)(F)F)Cc2cnn(-c3ccccc3F)c21]

Example 25

(R)-3,3,3-Trifluoro-1-[(S)-1-(2-fluoro-phenyl)-7-methyl-1,4,6,7-tetrahydro-pyrazolo[4,3-c]pyridin-5-yl]-2-hydroxy-2-methyl-propan-1-one ("A25")

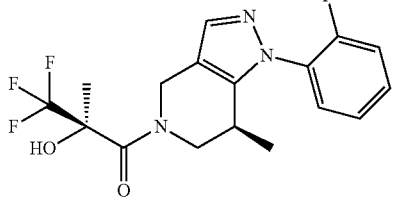

Preparation as described for "A9" (steps 9.1-9.4). The preparative separation of the diastereomers was performed by SFC (column: ChiralPak AS-H; eluent: CO$_2$:2-propanol-90:10). The combined fractions were evaporated to dryness. The oily residue was dissolved in acetonitrile, diluted with water and lyophilized.

"A24": 43 mg colorless solid; LC/MS, Rt: 2.02 min; (M+H) 372.1; $^1$H NMR (400 MHz, DMSO-$d_6$, 90° C.) δ 7.60-7.30 (m, 5H), 6.91 (s, 1H), 4.99-4.65 (m, 2H), 4.05-3.71 (m, 2H), 3.16-3.05 (m, 1H), 1.59 (s, 3H), 0.81 (d, J=6.8 Hz, 3H).

"A25": 45 mg colorless solid; LC/MS, Rt: 2.03 min; (M+H) 372.1; $^1$H NMR (400 MHz, DMSO-$d_6$, 90° C.) δ 7.61-7.32 (m, 5H), 6.90 (s, 1H), 4.95-4.66 (m, 2H), 4.13-3.60 (m, 2H), 3.15-3.04 (m, 1H), 1.59 (d, J=1.2 Hz, 3H), 0.80 (d, J=6.8 Hz, 3H).

Example 26

2-[(R)-7-Methyl-5-((R)-3,3,3-trifluoro-2-hydroxy-2-methyl-propionyl)-4,5,6,7-tetrahydro-pyrazolo[4,3-c]pyridin-1-yl]-benzonitrile ("A26")

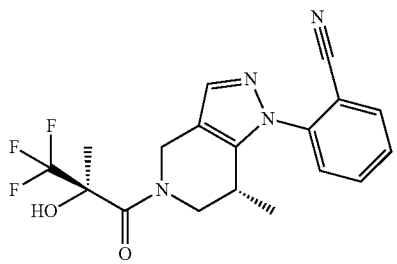 [SMILES: C[C@@H]1CN(C(=O)[C@@](C)(O)C(F)(F)F)Cc2cnn(-c3ccccc3C#N)c21]

Example 27

2-[(S)-7-Methyl-5-((R)-3,3,3-trifluoro-2-hydroxy-2-methyl-propionyl)-4,5,6,7-tetrahydro-pyrazolo[4,3-c]pyridin-1-yl]-benzonitrile ("A27")

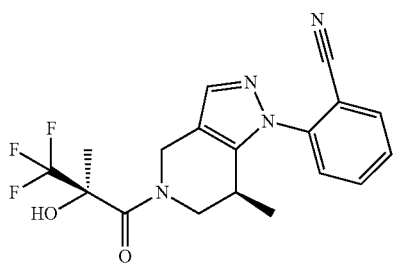 [SMILES: C[C@H]1CN(C(=O)[C@@](C)(O)C(F)(F)F)Cc2cnn(-c3ccccc3C#N)c21]

Preparation as described for "A9" (steps 9.1-9.4). The preparative separation of the diastereomers was performed by SFC (column: ChiralPak AD-H; eluent: CO$_2$:methanol (containing 0.5% diethylamine)-85:15). The combined fractions were evaporated to dryness. The oily residue was dissolved in acetonitrile, diluted with water and lyophilized.

"A26": 23 mg yellow solid; LC/MS, Rt: 2.03 min; (M+H) 379.1; $^1$H NMR (400 MHz, DMSO-$d_6$, 90° C.) δ 8.65 (s, 1H), 8.24 (dt, J=8.3, 1.1 Hz, 1H), 7.85 (dt, J=8.7, 0.9 Hz, 1H), 7.67-7.59 (m, 1H), 7.30 (ddd, J=7.9, 6.8, 0.9 Hz, 1H), 7.04 (s, 1H), 4.83-4.63 (m, 2H), 3.96-3.85 (m, 1H), 3.71-3.56 (m, 1H), 3.08-2.94 (m, 1H), 1.63 (d, J=1.2 Hz, 3H), 1.50 (d, J=6.9 Hz, 3H).

"A27": 32 mg yellow solid; LC/MS, Rt: 2.06 min; (M+H) 379.1; $^1$H NMR (400 MHz, DMSO-$d_6$, 90° C.) δ 8.64 (s, 1H), 8.24 (dd, J=8.3, 1.2 Hz, 1H), 7.85 (dd, J=8.7, 1.0 Hz, 1H), 7.63 (ddd, J=8.4, 6.7, 1.2 Hz, 1H), 7.34-7.27 (m, 1H), 7.08 (s, 1H), 4.86-4.67 (m, 2H), 3.96-3.87 (m, 1H), 3.65-3.50 (m, 1H), 3.13-3.02 (m, 1H), 1.68 (d, J=1.2 Hz, 3H), 1.50 (d, J=6.9 Hz, 3H).

Example 28

(R)-3,3,3-Trifluoro-2-hydroxy-2-methyl-1-((R)-7-methyl-1,4,6,7-tetrahydro-pyrazolo[4,3-c]pyridin-5-yl)-propan-1-one ("A28")

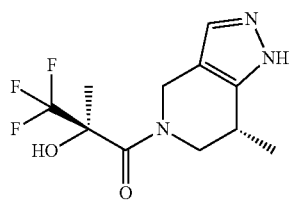 [SMILES: C[C@@H]1CN(C(=O)[C@@](C)(O)C(F)(F)F)Cc2cn[nH]c21]

Example 29

(R)-3,3,3-Trifluoro-2-hydroxy-2-methyl-1-((S)-7-methyl-1,4,6,7-tetrahydro-pyrazolo[4,3-c]pyridin-5-yl)-propan-1-one ("A29")

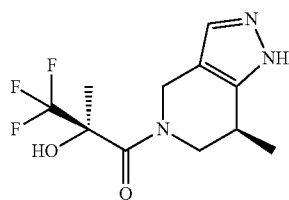 [SMILES: C[C@H]1CN(C(=O)[C@@](C)(O)C(F)(F)F)Cc2cn[nH]c21]

Preparation as described for "A9" (steps 9.1-9.4). The preparative separation of the diastereomers was performed by preparative HPLC (Agilent 1260; column: Waters SunFire C18, 5 μm, 30×150 mm). The combined fractions were evaporated to an aqueous residue, which was rendered basic with saturated NaHCO₃ solution and extracted with ethyl acetate. The combined organic layers were washed with brine, dried with Na₂SO₄, filtered and evaporated to dryness. The oily residue was dissolved in acetonitrile, diluted with water and lyophilized.

"A28": 30 mg colorless solid; LC/MS, Rt: 1.42 min; (M+H) 278.1;
"A29": 34 mg colorless solid; LC/MS, Rt: 1.46 min; (M+H) 278.1.

Example 30

(R)-3,3,3-Trifluoro-2-hydroxy-1-[(R)-1-(6-methoxy-pyridin-3-yl)-7-methyl-1,4,6,7-tetrahydro-pyrazolo[4,3-c]pyridin-5-yl]-2-methyl-propan-1-one ("A30")

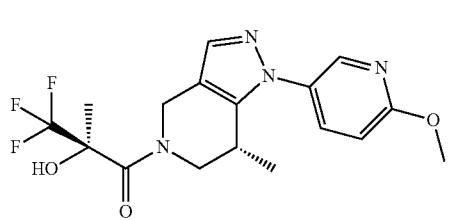 [SMILES: COc1ccc(-n2ncc3c2[C@H](C)CN(C(=O)[C@@](C)(O)C(F)(F)F)C3)cn1]

Example 31

(R)-3,3,3-Trifluoro-2-hydroxy-1-[(S)-1-(6-methoxy-pyridin-3-yl)-7-methyl-1,4,6,7-tetrahydro-pyrazolo[4,3-c]pyridin-5-yl]-2-methyl-propan-1-one ("A31")

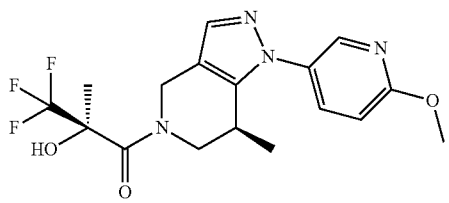 [SMILES: COc1ccc(-n2ncc3c2[C@@H](C)CN(C(=O)[C@@](C)(O)C(F)(F)F)C3)cn1]

Preparation as described for "A9" (steps 9.1-9.4). The preparative separation of the diastereomers was performed by preparative HPLC (column: LuxAmylose-2; eluent: n-heptane:2-propanol-70:30). The combined fractions were evaporated to dryness. The oily residue was dissolved in acetonitrile, diluted with water and lyophilized.

"A30": 87 mg colorless solid; LC/MS, Rt: 1.93 min; (M+H) 385.1; ¹H NMR (400 MHz, DMSO-d₆, 90° C.) δ 8.32 (d, J=2.7 Hz, 1H), 7.85 (dd, J=8.8, 2.7 Hz, 1H), 7.54 (s, 1H), 6.95 (d, J=8.8 Hz, 1H), 6.89 (s, 1H), 5.09-4.80 (m, 1H), 4.66 (d, J=15.7 Hz, 1H), 4.02-3.92 (m, 4H), 3.87-3.71 (m, 1H), 3.38-3.28 (m, 1H), 1.60 (d, J=1.2 Hz, 3H), 0.88 (d, J=6.8 Hz, 3H).

"A31": 82 mg colorless solid; LC/MS, Rt: 1.93 min; (M+H) 385.1; ¹H NMR (400 MHz, DMSO-d₆, 90° C.) δ 8.32 (d, J=2.5 Hz, 1H), 7.85 (dd, J=8.8, 2.8 Hz, 1H), 7.54 (s, 1H), 6.95 (d, J=8.7 Hz, 1H), 6.89 (s, 1H), 5.05-4.77 (m, 1H), 4.68 (d, J=15.7 Hz, 1H), 4.02-3.77 (m, 5H), 3.39-3.27 (m, 1H), 1.59 (d, J=1.1 Hz, 3H), 0.88 (d, J=6.9 Hz, 3H).

Example 32

(R)-3,3,3-Trifluoro-1-[(R)-1-(3-fluoro-pyridin-2-yl)-7-methyl-1,4,6,7-tetrahydro-pyrazolo[4,3-c]pyridin-5-yl]-2-hydroxy-2-methyl-propan-1-one ("A32")

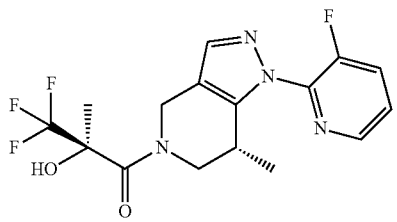 [SMILES: C[C@@H]1CN(C(=O)[C@@](C)(O)C(F)(F)F)Cc2cnn(-c3ncccc3F)c21]

Example 33

(R)-3,3,3-Trifluoro-1-[(S)-1-(3-fluoro-pyridin-2-yl)-7-methyl-1,4,6,7-tetrahydro-pyrazolo[4,3-c]pyridin-5-yl]-2-hydroxy-2-methyl-propan-1-one ("A33")

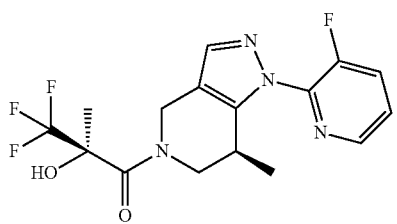 [SMILES: C[C@H]1CN(C(=O)[C@@](C)(O)C(F)(F)F)Cc2cnn(-c3ncccc3F)c21]

Preparation as described for "A9" (steps 9.1-9.4). The preparative separation of the diastereomers was performed by preparative HPLC (column: ChiralPak AD-H; eluent: n-heptane:2-propanol-85:15). The combined fractions were evaporated to dryness. The oily residue was dissolved in acetonitrile, diluted with water and lyophilized.

"A32": 66 mg colorless solid; LC/MS, Rt: 1.82 min; (M+H) 373.1; $^1$H NMR (400 MHz, DMSO-$d_6$, 90° C.) δ 8.41 (dt, J=4.7, 1.2 Hz, 1H), 7.97 (ddd, J=10.0, 8.3, 1.5 Hz, 1H), 7.65-7.55 (m, 2H), 6.93 (s, 1H), 5.07-4.68 (m, 2H), 3.97-3.77 (m, 2H), 3.44-3.34 (m, 1H), 1.60 (d, J=1.3 Hz, 4H), 0.89 (d, J=6.8 Hz, 4H).

"A33": 65 mg colorless solid; LC/MS, Rt: 1.83 min; (M+H) 373.1; $^1$H NMR (400 MHz, DMSO-$d_6$, 90° C.) δ 8.41 (dt, J=4.6, 1.2 Hz, 1H), 7.98 (ddd, J=10.1, 8.3, 1.4 Hz, 1H), 7.66-7.56 (m, 2H), 6.92 (s, 1H), 5.00-4.73 (m, 2H), 4.10-3.72 (m, 2H), 3.44-3.33 (m, 1H), 1.59 (d, J=1.1 Hz, 3H), 0.88 (d, J=6.8 Hz, 3H).

Example 34

(R)-1-[(R)-1-(3,5-Difluoro-pyridin-2-yl)-7-methyl-1,4,6,7-tetrahydro-pyrazolo[4,3-c]pyridin-5-yl]-3,3,3-trifluoro-2-hydroxy-2-methyl-propan-1-one ("A34")

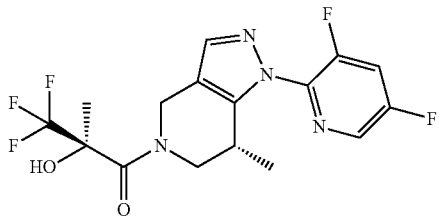 [SMILES: C[C@@H]1CN(C(=O)[C@@](C)(O)C(F)(F)F)Cc2cnn(-c3ncc(F)cc3F)c21]

Example 35

(R)-1-[(S)-1-(3,5-Difluoro-pyridin-2-yl)-7-methyl-1,4,6,7-tetrahydro-pyrazolo[4,3-c]pyridin-5-yl]-3,3,3-trifluoro-2-hydroxy-2-methyl-propan-1-one ("A35")

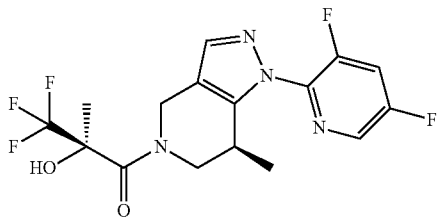 [SMILES: C[C@H]1CN(C(=O)[C@@](C)(O)C(F)(F)F)Cc2cnn(-c3ncc(F)cc3F)c21]

Preparation as described for "A9" (steps 9.1-9.4). The preparative separation of the diastereomers was performed by SFC (column: ChiralPak AS-H; eluent: CO$_2$:2-propanol (containing 0.5% diethylamine)-90:10). The combined fractions were evaporated to dryness. The oily residue was dissolved in acetonitrile, diluted with water and lyophilized.

"A34": 35 mg colorless solid; LC/MS, Rt: 1.94 min; (M+H) 391.1; $^1$H NMR (400 MHz, DMSO-$d_6$, 90° C., TFA) δ 8.37 (d, J=2.4 Hz, 1H), 7.90 (dd, J=10.1, 7.9 Hz, 1H), 7.59 (s, 1H), 5.06-4.69 (m, 2H), 4.02-3.80 (m, 2H), 3.44-3.31 (m, 1H), 1.63 (s, 3H), 0.91 (d, J=6.8 Hz, 3H).

"A35": 33 mg colorless solid; LC/MS, Rt: 1.95 min; (M+H) 391.1; $^1$H NMR (400 MHz, DMSO-$d_6$, 90° C.) δ 8.55-8.37 (m, 1H), 8.14 (ddd, J=9.8, 8.3, 2.5 Hz, 1H), 7.61 (s, 1H), 6.90 (s, 1H), 5.03-4.56 (m, 2H), 4.08-3.61 (m, 2H), 3.41-3.20 (m, 1H), 1.57 (s, 3H), 0.86 (d, J=6.8 Hz, 3H).

Example 36

(R)-3,3,3-Trifluoro-1-[(R)-1-(5-fluoro-2-methoxy-pyrimidin-4-yl)-7-methyl-1,4,6,7-tetrahydro-pyrazolo[4,3-c]pyridin-5-yl]-2-hydroxy-2-methyl-propan-1-one ("A36")

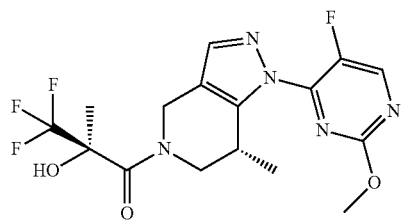 [SMILES: COc1ncc(F)c(-n2ncc3c2[C@H](C)CN(C(=O)[C@@](C)(O)C(F)(F)F)C3)n1]

Example 37

(R)-3,3,3-Trifluoro-1-[(S)-1-(5-fluoro-2-methoxy-pyrimidin-4-yl)-7-methyl-1,4,6,7-tetrahydro-pyrazolo[4,3-c]pyridin-5-yl]-2-hydroxy-2-methyl-propan-1-one ("A37")

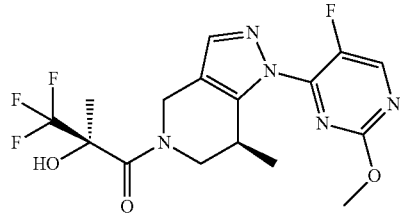 [SMILES: COc1ncc(F)c(-n2ncc3c2[C@@H](C)CN(C(=O)[C@@](C)(O)C(F)(F)F)C3)n1]

Preparation as described for "A9" (steps 9.1-9.4). The preparative separation of the diastereomers was performed by SFC (column: ChiralPak AD-H; eluent: CO$_2$:methanol (containing 0.5% diethylamine)-85:15). The combined fractions were evaporated to dryness. The oily residue was dissolved in acetonitrile, diluted with water and lyophilized.

"A36": 46 mg colorless solid; LC/MS, Rt: 1.99 min; (M+H) 404.1; $^1$H NMR (400 MHz, DMSO-$d_6$, 90° C., TFA) δ 8.62 (d, J=3.9 Hz, 1H), 8.39 (s, 1H), 5.24 (d, J=16.4 Hz, 1H), 4.68-4.36 (m, 2H), 3.99 (s, 3H), 3.28 (dd, J=13.1, 9.0 Hz, 1H), 3.20-3.05 (m, 1H), 1.61 (d, J=1.2 Hz, 3H), 1.29 (d, J=6.9 Hz, 3H).

"A37": 48 mg colorless solid; LC/MS, Rt: 1.96 min; (M+H) 404.1; $^1$H NMR (400 MHz, DMSO-$d_6$) δ 8.76 (d, J=3.9 Hz, 1H), 8.50 (s, 1H), 7.33-7.06 (m, 1H), 5.41-5.02 (m, 1H), 5.02-4.51 (m, 1H), 4.24-3.89 (m, 4H), 3.39-2.93 (m, 2H), 1.72-1.38 (m, 3H), 1.24 (d, J=6.7 Hz, 3H).

Example 38

(R)-3,3,3-Trifluoro-2-hydroxy-1-[(R)-1-(4-hydroxy-cyclohexyl)-7-methyl-1,4,6,7-tetrahydro-pyrazolo[4,3-c]pyridin-5-yl]-2-methyl-propan-1-one ("A38")

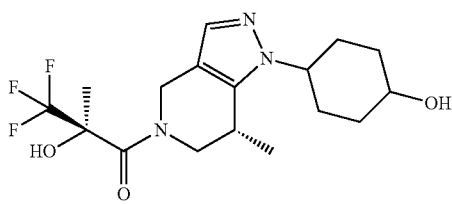 [SMILES: C[C@@H]1CN(C(=O)[C@@](C)(O)C(F)(F)F)Cc2cnn(C3CCC(O)CC3)c21]

Example 39

(R)-3,3,3-Trifluoro-2-hydroxy-1-[(S)-1-(4-hydroxy-cyclohexyl)-7-methyl-1,4,6,7-tetrahydro-pyrazolo[4,3-c]pyridin-5-yl]-2-methyl-propan-1-one ("A39")

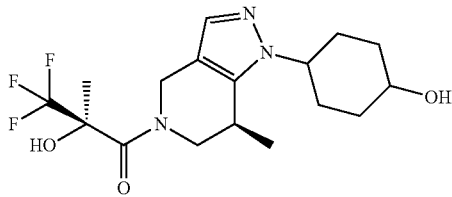 [SMILES: C[C@H]1CN(C(=O)[C@@](C)(O)C(F)(F)F)Cc2cnn(C3CCC(O)CC3)c21]

Preparation as described for "A9" (steps 9.1-9.4). The preparative separation of the diastereomers was performed by SFC (column: ChiralCel OJ-H; eluent: $CO_2$:methanol-90:10). The combined fractions were evaporated to dryness. The oily residue was dissolved in acetonitrile, diluted with water and lyophilized.

"A38": 6 mg colorless solid; LC/MS, Rt: 1.66 min; (M+H) 376.2; $^1$H NMR (400 MHz, DMSO-$d_6$, 90° C.) δ 7.21 (s, 1H), 6.82 (s, 1H), 5.21-4.95 (m, 1H), 4.39-4.25 (m, 2H), 4.15-4.05 (m, 1H), 3.98 (tt, J=10.7, 3.5 Hz, 1H), 3.90-3.79 (m, 1H), 3.46-3.29 (m, 1H), 3.20-3.04 (m, 1H), 2.41-2.09 (m, 2H), 1.90-1.68 (m, 2H), 1.66-1.42 (m, 7H), 1.14 (d, J=6.8 Hz, 3H).

"A39": 7 mg colorless solid; LC/MS, Rt: 1.65 min; (M+H) 376.2; $^1$H NMR (400 MHz, DMSO-$d_6$, 90° C.) δ 7.22 (s, 1H), 6.80 (s, 1H), 5.24-4.90 (m, 1H), 4.42-4.18 (m, 2H), 4.08 (d, J=2.8 Hz, 1H), 3.99 (tt, J=10.9, 3.7 Hz, 1H), 3.91-3.79 (m, 1H), 3.48-3.30 (m, 1H), 3.21-3.08 (m, 1H), 2.41-2.11 (m, 2H), 1.88-1.73 (m, 2H), 1.68-1.44 (m, 7H), 1.14 (d, J=6.8 Hz, 3H).

Example 40

(R)-3,3,3-Trifluoro-1-[(R)-1-(5-fluoro-pyridin-2-yl)-7-methyl-1,4,6,7-tetrahydro-pyrazolo[4,3-c]pyridin-5-yl]-2-hydroxy-2-methyl-propan-1-one ("A40")

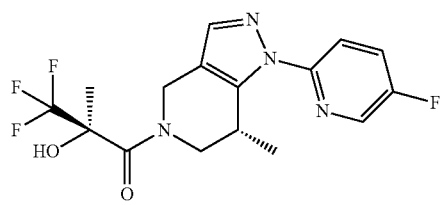 [SMILES: C[C@@H]1CN(C(=O)[C@@](C)(O)C(F)(F)F)Cc2cnn(-c3ccc(F)cn3)c21]

Example 41

(R)-3,3,3-Trifluoro-1-[(S)-1-(5-fluoro-pyridin-2-yl)-7-methyl-1,4,6,7-tetrahydro-pyrazolo[4,3-c]pyridin-5-yl]-2-hydroxy-2-methyl-propan-1-one ("A41")

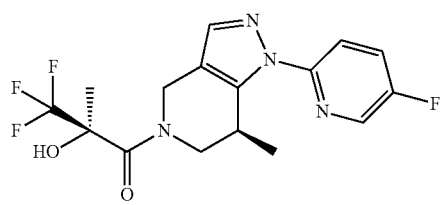 [SMILES: C[C@H]1CN(C(=O)[C@@](C)(O)C(F)(F)F)Cc2cnn(-c3ccc(F)cn3)c21]

Preparation as described for "A9" (steps 9.1-9.4). The preparative separation of the diastereomers was performed by SFC (column: ChiralPak AS-H; eluent: $CO_2$:methanol-85:15). The combined fractions were evaporated to dryness. The oily residue was dissolved in acetonitrile, diluted with water and lyophilized.

"A40": 44 mg colorless solid; LC/MS, Rt: 2.17 min; (M+H) 373.2; $^1$H NMR (400 MHz, DMSO-$d_6$, 90° C.) δ 8.47-8.40 (m, 1H), 7.94-7.83 (m, 2H), 7.60 (s, 1H), 6.91 (s, 1H), 5.40-5.02 (s, 1H), 4.49-4.33 (m, 2H), 3.84-3.74 (m, 1H), 3.59-3.37 (m, 1H), 1.62 (d, J=1.1 Hz, 3H), 1.14 (d, J=6.7 Hz, 3H).

"A41": 35 mg colorless solid; LC/MS, Rt: 2.16 min; (M+H) 373.2; $^1$H NMR (400 MHz, DMSO-$d_6$, 90° C.) δ 8.44 (d, J=2.8 Hz, 1H), 7.95-7.84 (m, 2H), 7.61 (s, 1H), 6.88 (s, 1H), 5.30-5.00 (m, 1H), 4.48 (d, J=16.2 Hz, 1H), 4.28 (dd, J=12.9, 3.8 Hz, 1H), 3.84-3.73 (m, 1H), 3.67-3.43 (m, 1H), 1.59 (s, 3H), 1.13 (d, J=6.7 Hz, 3H).

Example 42

1-[(R)-1-(4-Fluoro-phenyl)-7-methyl-1,4,6,7-tetrahydro-pyrazolo[4,3-c]pyridin-5-yl]-2-hydroxy-2-methyl-propan-1-one ("A42")

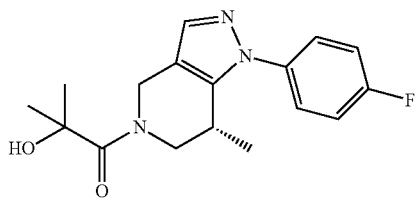 [SMILES: C[C@@H]1CN(C(=O)C(C)(C)O)Cc2cnn(-c3ccc(F)cc3)c21]

Preparation according to the alternative method described for the synthesis of "A14" and "A15". After separation of the enantiomeric Boc-protected cyclization products (step 12.1) BOC-deprotection and acylation with 2-hydroxy-2-methyl-propionic acid was performed as described for "A9" (steps 9.3-9.4).

"A42": 30 mg colorless solid; LC/MS, Rt: 1.82 min; (M+H) 318.2; $^1$H NMR (400 MHz, DMSO-$d_6$, 90° C.) δ 7.60-7.54 (m, 2H), 7.52 (s, 1H), 7.36-7.28 (m, 2H), 5.18 (s, 1H), 4.85 (d, J=15.8 Hz, 1H), 4.70 (d, J=15.8 Hz, 1H), 3.95-3.78 (m, 2H), 3.40-3.28 (m, 1H), 1.40 (s, 3H), 1.39 (s, 3H), 0.86 (d, J=6.8 Hz, 3H).

General reaction scheme for manufacturing compounds of formula Ia in which X=CH, Y=N and R$^2$ denotes H

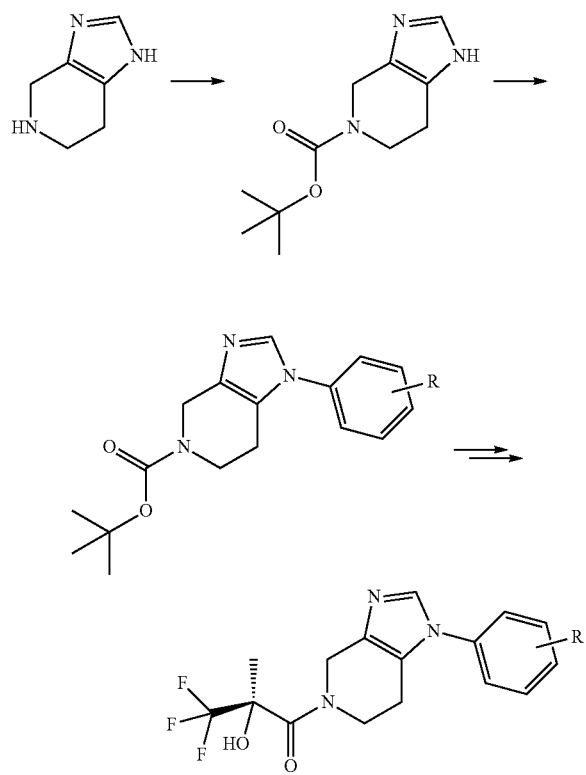

Example 43

(R)-3,3,3-Trifluoro-2-hydroxy-2-methyl-1-(3-phenyl-3,4,6,7-tetrahydro-imidazo[4,5-c]pyridin-5-yl)-propan-1-one ("A43")

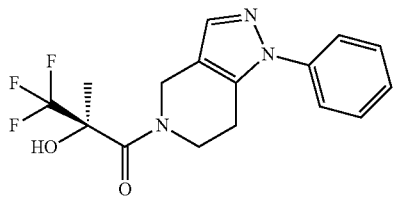 [SMILES: C[C@@](O)(C(=O)N1CCc2c(cnn2-c2ccccc2)C1)C(F)(F)F]

43.1 1,4,6,7-Tetrahydro-imidazo[4,5-c]pyridine-5-carboxylic acid tert-butyl ester 4,5,6,7-Tetrahydro-1 H-imidazo[4,5-c]pyridine (500.0 mg; 4.060 mmol) was suspended in dry THF (10.0 mL) and DIPEA (1.59 mL; 9.338 mmol) and 4-(dimethylamino) pyridine (99.2 mg; 0.812 mmol) were added followed by the addition of di-tert-butyl dicarbonate (1.95 g; 8.932 mmol). The reaction mixture was diluted with methanol (2.0 mL) and stirred for 16 h at room temperature. The reaction mixture was diluted with ethyl acetate, washed with 0.5 N HCl, saturated NaHCO$_3$ solution and brine, dried with Na$_2$SO$_4$, filtered by suction and evaporated to dryness. The residue was suspended in methanol (5.0 mL) and treated with 1 N sodium hydroxide solution (0.32 mL; 8.323 mmol). The reaction mixture was stirred for 20 min at room temperature and concentrated under vacuum to an aqueous residue. This residue was diluted with water and extracted with ethyl acetate. The combined organic layers were washed with brine, dried with Na$_2$SO$_4$, filtered by suction and evaporated to dryness. Yield: 682.5 mg (75%) yellow oil

43.2 1-Phenyl-1,4,6,7-tetrahydro-imidazo[4,5-c] pyridine-5-carboxylic acid tert-butyl ester 1,4,6,7-Tetrahydro-imidazo[4,5-c]pyridine-5-carboxylic acid tert-butyl ester (219.0 mg; 0.981 mmol), benzeneboronic acid (239.2 mg; 1.962 mmol) and copper(II)acetate (89.1 mg; 0.490 mmol) were suspended under argon in dry dichloromethane (4.0 mL). Dry pyridine (158 μl; 1.962 mmol) was added and the dark blue reaction mixture was stirred for 43 h at room temperature. Further benzeneboronic acid (239.2 mg; 1.962 mmol), copper(II)acetate (89.1 mg; 0.490 mmol) and dry pyridine (158 μl; 1.962 mmol) was added under argon and the mixture was stirred for 21 h at room temperature. The reaction mixture was diluted with dichloromethane, washed with 15% ammonia solution water and brine, dried with Na$_2$SO$_4$, filtered by suction and evaporated to dryness. The oily residue was purified by chromatography (Companion RF; 24 g Si50 silica gel column) and the isomers were separated by preparative HPLC (Agilent 1260; column: Waters SunFire C18 5 μm 30×150 mm). The combined fractions were evaporated to an aqueous residue, rendered basic with saturated NaHCO$_3$ solution and extracted with ethyl acetate. The combined organic layers were washed with brine, dried with Na$_2$SO$_4$, filtered and evaporated to dryness. Yield: 81 mg (28%) colorless oil; LC/MS, Rt: 1.65 min; (M+H) 300.2.

Steps 43.3 (BOC-deprotection) and 43.4 (acylation) were performed as described for example 9 (steps 9.3-9.4). Yield: 80.5 mg (78%) colorless solid; LC/MS, Rt: 1.38 min; (M+H) 340.1; $^1$H NMR (400 MHz, DMSO-$d_6$, 90° C.) δ 7.80 (s, 1H), 7.59-7.50 (m, 2H), 7.48-7.41 (m, 3H), 6.89 (s, 1H), 4.83-4.62 (m, 2H), 4.14-3.93 (m, 2H), 2.73 (t, J=5.8 Hz, 2H), 1.60 (s, 3H).

Example 44

(R)-3,3,3-Trifluoro-1-[1-(4-fluoro-phenyl)-1,4,6,7-tetrahydro-imidazo[4,5-c]pyridin-5-yl]-2-hydroxy-2-methyl-propan-1-one ("A44")

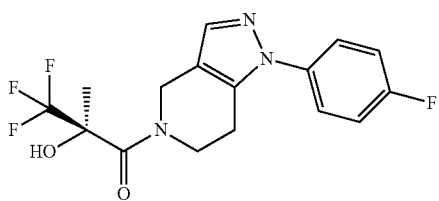 [SMILES: C[C@@](O)(C(=O)N1CCc2c(cnn2-c2ccc(F)cc2)C1)C(F)(F)F]

Preparation as described for example 43 (steps 43.1-43.4). Yield: 33 mg (63%) colorless solid; LC/MS, Rt: 1.46 min; (M+H) 358.2; $^1$H NMR (400 MHz, DMSO-$d_6$) δ 7.86 (s, 1H), 7.56-7.49 (m, 2H), 7.42-7.33 (m, 2H), 7.21-7.08 (m, 1H), 5.05-4.82 (m, 1H), 4.56-4.38 (m, 1H), 4.25-3.97 (m, 1H), 3.93-3.68 (m, 1H), 2.82-2.57 (m, 2H), 1.66-1.43 (m, 3H).

Example 45

(R)-1-[1-(4-Chloro-phenyl)-1,4,6,7-tetrahydro-imidazo[4,5-c]pyridin-5-yl]-3,3,3-trifluoro-2-hydroxy-2-methyl-propan-1-one ("A45")

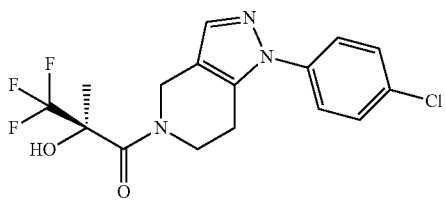 [SMILES: C[C@@](O)(C(=O)N1CCc2c(cnn2-c2ccc(Cl)cc2)C1)C(F)(F)F]

Preparation as described for "A43" (steps 43.1-43.4). Yield: 39 mg (89%) colorless solid; LC/MS, Rt: 1.65 min; (M+H) 374.1; $^1$H NMR (400 MHz, DMSO-$d_6$) δ 7.91 (s, 1H), 7.63-7.56 (m, 2H), 7.55-7.48 (m, 2H), 7.15 (s, 1H), 5.03-4.41 (m, 2H), 4.27-3.68 (m, 2H), 2.85-2.61 (m, 2H), 1.67-1.47 (m, 3H).

General reaction scheme for manufacturing compounds of formula Ia in which X=N, Y=N and R$^2$ denotes H

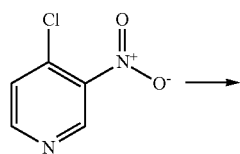

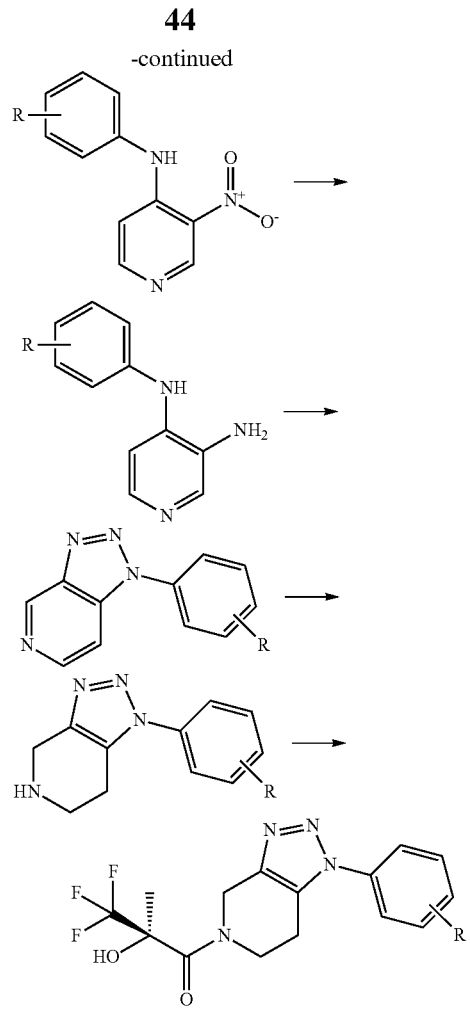

Example 46

(R)-3,3,3-Trifluoro-2-hydroxy-2-methyl-1-(1-phenyl-1,4,6,7-tetrahydro-[1,2,3]triazolo[4,5-c]pyridin-5-yl)-propan-1-one ("A46")

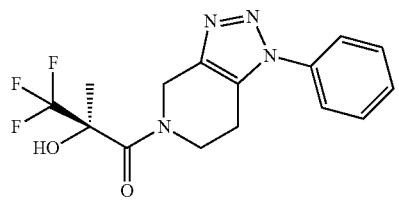 [SMILES: C[C@@](O)(C(=O)N1CCc2c(nnn2-c2ccccc2)C1)C(F)(F)F]

46.1 (3-Nitro-pyridin-4-yl)-phenyl-amine

4-Chloro-3-nitro-pyridine (1.50 g; 9.177 mmol), aniline (1.02 mL; 11.013 mmol) and anhydrous sodium acetate (3.76 g; 45.887 mmol) were suspended in glacial acetic acid (7.50 mL) and stirred at 130° C. for 14 h. The mixture was cooled to room temperature and poured into water, neutralized with aqueous NaHCO$_3$-solution and extracted with dichloromethane. The combined organic layers were dried over sodium sulfate, filtered and concentrated in vacuo. The residue was purified by flash chromatography (Combi-FlashRF 200). Yield: 1.90 g (96%) yellow solid; LC/MS, Rt: 1.40 min; (M+H) 216.1.

46.2 N4-Phenyl-pyridine-3,4-diamine

Compound 46.1 (2.30 g; 10.645 mmol) was hydrogenated at room temperature in THF (30.0 mL) for 14 h using Pd—C (5%). The solution was filtered, evaporated to dryness and the residue was used in the next step without further purification. Yield: 1.91 g (97%) colorless solid; LC/MS, Rt: 1.13 min; (M+H) 186.1.

46.3 1-Phenyl-1H-[1,2,3]triazolo[4,5-c]pyridine

Compound 46.2 (500.0 mg; 2.683 mmol) was dissolved in hydrochloric acid (40.3 mL; 4.025 mmol) and cooled to 0° C. Sodium nitrite (280.5 mg; 4.025 mmol), dissolved in water (5.0 mL), was added slowly while a colorless precipitate was formed. The suspension was stirred at 0° C. for 30 min and then allowed to warm up to room temperature for 14 h. The reaction mixture was diluted with saturated aqueous NaHCO$_3$-solution and extracted with ethyl acetate. The combined organic layers were washed with brine, dried over sodium sulfate, filtered and concentrated in vacuo. The residue was purified by flash chromatography (Combi-FlashRF 200). Yield: 496 mg (94%) beige solid; LC/MS, Rt: 1.71 min; (M+H) 197.1.

46.4 1-Phenyl-4,5,6,7-tetrahydro-1H-[1,2,3]triazolo[4,5-c]pyridine

Compound 46.3 (299.0 mg; 1.524 mmol) was dissolved in methanol (10.0 mL) and hydrogenated over Pd—C (5%) at room temperature and 2.9-3.2 bar for 14 h. The reaction was filtered and evaporated to dryness. Yield: 305 mg (100%) colorless oil; LC/MS, Rt: 0.89 min; (M+H) 201.1.

46.5 (R)-3,3,3-Trifluoro-2-hydroxy-2-methyl-1-(1-phenyl-1,4,6,7-tetrahydro-[1,2,3]triazolo[4,5-c]pyridin-5-yl)-propan-1-one ("A46")

Acylation was performed as described for "A9" (step 9.4). Yield: 378 mg (72%) colorless solid; LC/MS, Rt: 1.88 min; (M+H) 341.1; $^1$H NMR (400 MHz, DMSO-d$_6$, 90° C.) δ 7.68-7.62 (m, 2H), 7.62-7.56 (m, 2H), 7.56-7.48 (m, 1H), 6.97 (s, 1H), 4.92 (s, 2H), 4.16-4.04 (m, 1H), 4.04-3.94 (m, 1H), 2.94 (t, J=5.7 Hz, 2H), 1.61-1.57 (m, 3H).

Example 47

(R)-3,3,3-Trifluoro-1-[1-(4-fluoro-phenyl)-1,4,6,7-tetrahydro-[1,2,3]triazolo[4,5-c]pyridin-5-yl]-2-hydroxy-2-methyl-propan-1-one ("A47")

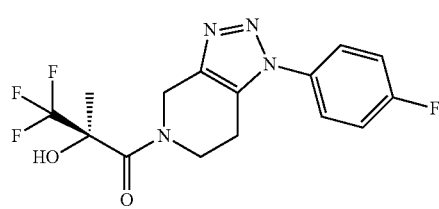 [SMILES: C[C@@](O)(C(=O)N1CCc2c(nnn2-c2ccc(F)cc2)C1)C(F)(F)F]

Preparation as described for "A46" (steps 46.1-46.5). Yield: 89 mg (70%) colorless solid; LC/MS, Rt: 1.93 min; (M+H) 359.0; $^1$H NMR (400 MHz, DMSO-d$_6$, 90° C.) δ 7.78-7.61 (m, 2H), 7.49-7.34 (m, 2H), 6.97 (s, 1H), 4.91 (s, br, 2H), 4.17-3.93 (m, 2H), 2.91 (t, J=5.7 Hz, 2H), 1.69-1.47 (m, 3H).

Example 48

(R)-3,3,3-Trifluoro-2-hydroxy-2-methyl-1-(3-phenyl-5,6-dihydro-8H-[1,2,4]triazolo[4,3-a]pyrazin-7-yl)-propan-1-one ("A48")

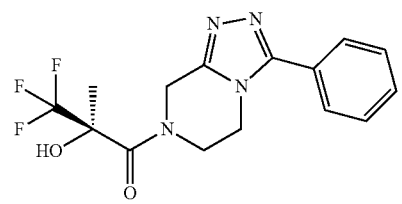 [SMILES: C[C@@](O)(C(=O)N1CCn2c(nnc2-c2ccccc2)C1)C(F)(F)F]

3-Phenyl-5,6,7,8-tetrahydro-[1,2,4]triazolo[4,3-a]pyrazine (60.0 mg; 0.300 mmol) was coupled with (R)-3,3,3-trifluoro-2-hydroxy-2-methyl-propionic acid (52.1 mg; 0.330 mmol) as described for "A9" (step 9.4). Yield: 78 mg (77%) colorless solid; LC/MS, Rt: 1.54 min; (M+H) 341.2; $^1$H NMR (400 MHz, DMSO-d$_6$, 80° C.) δ 7.79-7.71 (m, 2H), 7.58-7.48 (m, 3H), 7.14 (s, 1H), 5.22-4.95 (m, 2H), 4.33-4.03 (m, 4H), 1.60 (s, 3H).

Example 49

(R)-3,3,3-Trifluoro-2-hydroxy-2-methyl-1-(3-phenyl-5,6-dihydro-8H-imidazo[1,2-a]pyrazin-7-yl)-propan-1-one ("A49")

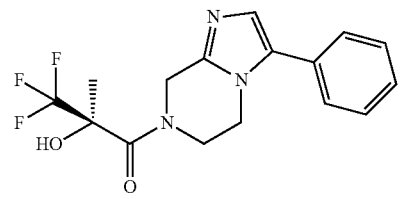 [SMILES: C[C@@](O)(C(=O)N1CCn2c(-c3ccccc3)cnc2C1)C(F)(F)F]

3-Phenyl-5,6,7,8-tetrahydro-imidazo[1,2-a]pyrazine (50.0 mg; 0.251 mmol) was coupled with (R)-3,3,3-trifluoro-2-hydroxy-2-methyl-propionic acid (43.6 mg; 0.276 mmol) as described for "A9" (step 9.4). Yield: 41 mg (49%) colorless solid; LC/MS, Rt: 1.36 min; (M+H) 340.2; $^1$H NMR (400 MHz, DMSO-d$_6$) δ 7.54-7.41 (m, 4H), 7.41-7.23 (m, 2H), 7.09 (s, 1H), 5.37-3.84 (m, 6H), 1.59 (s, 3H).

General reaction scheme for manufacturing compounds of formula Ib in which X=N, Y=CH and R$^2$ denotes H

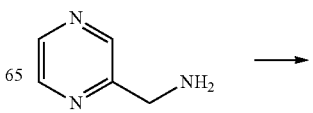

47

-continued

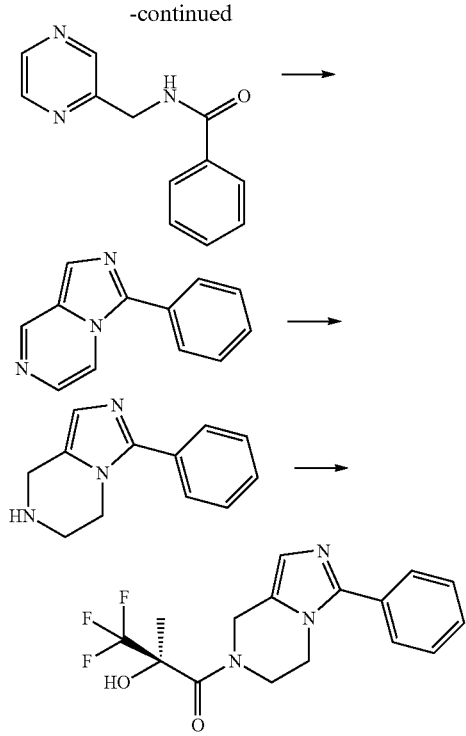

Example 50

(R)-3,3,3-Trifluoro-2-hydroxy-2-methyl-1-(3-phenyl-5,6-dihydro-8H-imidazo-[1,5-a]pyrazin-7-yl)-propan-1-one ("A50")

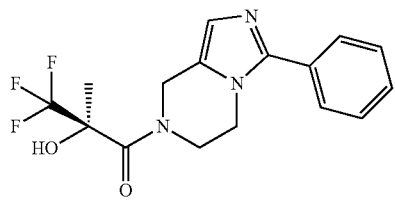 [SMILES: C[C@@](O)(C(=O)N1CCn2c(cnc2-c2ccccc2)C1)C(F)(F)F]

50.1 N-Pyrazin-2-ylmethyl-benzamide (Pyrazin-2-yl)methanamine (500.0 mg; 4.353 mmol) was dissolved in dichloromethane (20.0 mL) under argon and cooled to 0° C. N-Ethyldiisopropylamine (0.89 mL; 5.223 mmol) was added followed by the addition of benzoyl chloride (0.56 mL; 4.788 mmol). The reaction mixture was allowed to warm to room temperature and stirred for 18 h. The reaction mixture was diluted with saturated NaHCO₃ solution. The organic phase was separated and the aqueous layer was washed 3 times with dichloromethane. The combined organic layers were dried over sodium sulfate, filtered and evaporated to dryness. The residue was purified by flash chromatography (Companion RF; 40 g Si50 silica gel column). Yield: 895 mg (96%) yellow solid; LC/MS, Rt: 1.36 min; (M+H) 214.1.

48

50.2 3-Phenylimidazo[1,5-a]pyrazine

N-Pyrazin-2-ylmethyl-benzamide (300.0 mg; 1.353 mmol) was dissolved in dry acetonitrile (25.0 mL). POCl₃ (1.24 mL; 13.534 mmol) was added under nitrogen atmosphere and the reaction mixture was heated at 85° C. for 4 h. The reaction mixture was cooled to room temperature and evaporated to dryness. The residue was diluted in a mixture of DCM, ice water and NaHCO₃ solution. The organic layer was separated and the aqueous layer was extracted with dichloromethane. The combined organic layers were dried over sodium sulfate, filtered and evaporated to dryness. Yield: 244 mg (92%) brown oil; LC/MS, Rt: 1.40 min; (M+H) 196.1.

50.3 3-Phenyl-5,6,7,8-tetrahydro-imidazo[1,5-a]pyrazine

Compound 50.2 (244.0 mg; 1.249 mmol) was dissolved in methanol (10.0 mL) and hydrogenated over Pd—C (5%) at room temperature and 2.8 bar for 14 h. The reaction was filtered and evaporated to dryness. Yield: 233 mg (94%) yellow oil; LC/MS, Rt: 0.32 min; (M+H) 200.1.

50.4 (R)-3,3,3-Trifluoro-2-hydroxy-2-methyl-1-(3-phenyl-5,6-dihydro-8H-imidazo[1,5-a]pyrazin-7-yl)-propan-1-one ("A50")

Compound 50.3 (233.0 mg; 1.169 mmol) was coupled with (R)-3,3,3-trifluoro-2-hydroxy-2-methyl-propionic acid (43.6 mg; 0.276 mmol) as described for example 9 (step 9.4). Yield: 171 mg (43%) colorless solid; LC/MS, Rt: 1.25 min; (M+H) 340.1; ¹H NMR (400 MHz, DMSO-d₆, 90° C.) δ 7.73-7.68 (m, 2H), 7.51-7.45 (m, 2H), 7.44-7.39 (m, 1H), 7.02 (s, 1H), 6.94-6.90 (m, 1H), 4.97 (s, 2H), 4.22 (t, J=5.3 Hz, 2H), 4.18-4.05 (m, 2H), 1.66-1.58 (m, 3H).

Example 51

(R)-3,3,3-Trifluoro-1-[3-(4-fluoro-phenyl)-5,6-dihydro-8H-imidazo[1,5-a]pyrazin-7-yl]-2-hydroxy-2-methyl-propan-1-one ("A51")

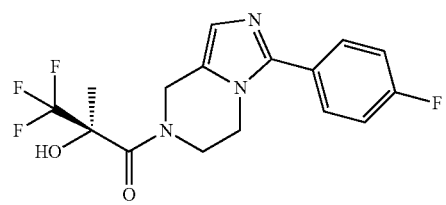 [SMILES: C[C@@](O)(C(=O)N1CCn2c(cnc2-c2ccc(F)cc2)C1)C(F)(F)F]

Preparation as described for "A50" (steps 50.1-50.4). Yield: 234 mg (65%) colorless solid; LC/MS, Rt: 1.34 min; (M+H) 358.0; ¹H NMR (400 MHz, DMSO-d₆, 90° C.) δ 7.73 (ddd, J=8.3, 5.3, 2.4 Hz, 2H), 7.27 (td, J=8.9, 2.1 Hz, 2H), 7.01 (s, 1H), 6.90 (s, 1H), 4.95 (s, 2H), 4.24-4.01 (m, 4H), 1.61 (s, 3H).

General reaction scheme for manufacturing compounds of formula Ib in which X=N, Y=CH and R² denotes CH₃

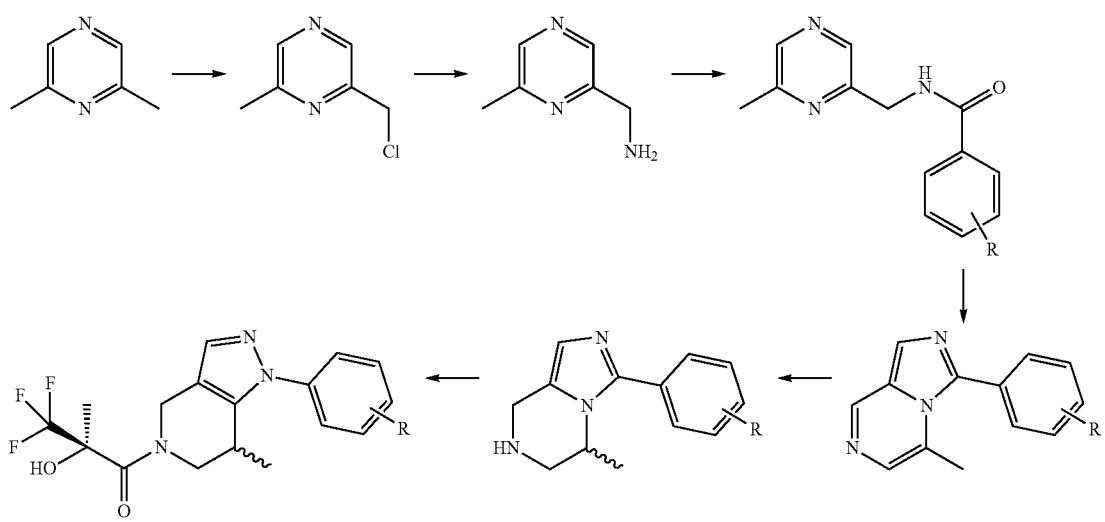

Example 52

(R)-3,3,3-Trifluoro-1-[(R)-3-(4-fluoro-phenyl)-5-methyl-5,6-dihydro-8H-imidazo[1,5-a]pyrazin-7-yl]-2-hydroxy-2-methyl-propan-1-one ("A52")

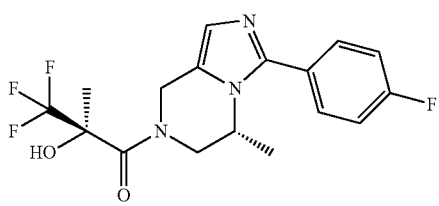 [SMILES: C[C@@H]1CN(C(=O)[C@@](C)(O)C(F)(F)F)Cc2cnc(-c3ccc(F)cc3)n21]

Example 53

(R)-3,3,3-Trifluoro-1-[(S)-3-(4-fluoro-phenyl)-5-methyl-5,6-dihydro-8H-imidazo[1,5-a]pyrazin-7-yl]-2-hydroxy-2-methyl-propan-1-one ("A53")

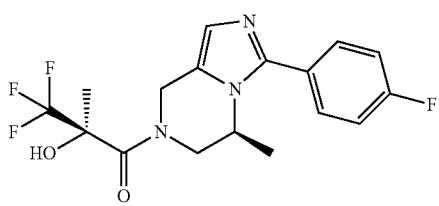 [SMILES: C[C@H]1CN(C(=O)[C@@](C)(O)C(F)(F)F)Cc2cnc(-c3ccc(F)cc3)n21]

52.1 2-Chloromethyl-6-methyl-pyrazine

To 2,6-dimethylpyrazine (500.0 mg; 4.623 mmol) and N-chlorosuccinimide (617.4 mg; 4.531 mmol) tetrachloromethane (12.5 mL) was added under nitrogen and the mixture was heated to reflux. Benzoyl benzenecarboperoxoate (22.2 mg; 0.077 mmol) was added and the colorless suspension was heated at 85° C. for 3 h. N-chlorosuccinimide (61.7 mg; 0.453 mmol) was added and the reaction was heated for another 2 h and then stirred at room temperature for 14 h. The reaction was diluted with water and extracted with dichloromethane. The combined organic layers were dried over sodium sulfate, filtered and concentrated in vacuo. The residue was purified by flash chromatography (CombiFlashRF 200). Yield: 328 mg (51%) colorless oil; LC/MS, Rt: 1.35 min; (M+H) 143.1/145.1.

52.2 2-(6-Methyl-pyrazin-2-ylmethyl)-isoindole-1,3-dione

Compound 52.1 (310.0 mg; 2.174 mmol), sodium hydrogen carbonate (219.0 mg; 2.609 mmol) and phthalimide potassium salt (403.0 mg; 2.174 mmol) was dissolved in DMF (4.0 mL) and the dark red/brown solution was stirred at room temperature for 14 h. The mixture was concentrated, diluted with water and extracted with ethyl acetate. The combined organic layers were washed with brine, dried over sodium sulfate, filtered and concentrated in vacuo. The residue was purified by flash chromatography (CombiFlashRF). Yield: 226 mg (41%) colorless solid; LC/MS, Rt: 1.74 min; (M+H) 254.1.

52.3 C-(6-Methyl-pyrazin-2-yl)-methylamine

To a suspension of 2-(6-methyl-pyrazin-2-ylmethyl)-isoindole-1,3-dione (1.57 g; 6.191 mmol) in ethanol (60.0 mL) hydrazinium hydroxide (2.41 mL; 49.531 mmol) was added slowly while stirring and the mixture was heated to 80° C. After 5 min a colorless solution was formed which turned into a colorless suspension after 30 min. The reaction mixture was refluxed for further 6 h, cooled to room temperature, diluted with water (80 mL) and 0.1 N NaOH (30 mL) and extracted with a mixture of dichloromethane-methanol (1/1). The combined organic layers were dried over sodium sulfate, filtered and concentrated in vacuo. Yield: 417 mg (55%) colorless oil; LC/MS, Rt: 0.33 min; (M+H) 124.2.

52.4 4-Fluoro-N-(6-methyl-pyrazin-2-ylmethyl)-benzamide

Compound 52.3 (416.0 mg; 3.378 mmol) was dissolved in dichloromethane (15.0 mL) and cooled in an ice bath.

N-ethyldiisopropylamine (0.69 mL; 4.053 mmol) and 4-fluorobenzoyl chloride (0.43 mL; 3.547 mmol) were added and the ice bath was removed. A yellow solution was formed and stirred for 4 h. The mixture was diluted with saturated aqueous NaHCO$_3$-solution and water. The organic phase was separated and the aqueous layer was washed with dichloromethane. The combined organic layers were dried over sodium sulfate, filtered and concentrated in vacuo. The crude product was purified by flash chromatography (CombiFlashRF 200). Yield: 728 mg (88%) yellow solid; LC/MS, Rt: 1.56 min; (M+H) 246.1.

52.5 3-(4-Fluoro-phenyl)-5-methyl-imidazo[1,5-a]pyrazine

Compound 52.4 (728.0 mg; 2.967 mmol) was dissolved in dry acetonitrile (40.1 mL). POCl$_3$ (2.77 mL; 29.669 mmol) was added. The orange mixture was stirred at 95° C. for 18 h. The reaction mixture was cooled to room temperature, cautiously diluted with water (150 mL) and neutralized with sodium bicarbonate. The organic phase was separated and the aqueous layer was washed with dichloromethane. The combined organic layers were dried over sodium sulfate, filtered and concentrated in vacuo. The crude residue was purified by flash chromatography (CombiFlashRF 200). Yield: 617 mg (91%) yellow solid; LC/MS, Rt: 1.47 min; (M+H) 228.1.

52.6 3-(4-Fluoro-phenyl)-5-methyl-5,6,7,8-tetrahydro-imidazo[1,5-a]pyrazine

Compound 52.5 (617.0 mg; 2.713 mmol) was dissolved in methanol (10.0 mL) and hydrogenated over Pd—C (5%) at room temperature and 3.0 bar for 4 h. The reaction was filtered and evaporated to dryness. Yield: 606 mg (97%) off-white oil; LC/MS, Rt: 0.34 min; (M+H) 232.2.

52.7 (R)-3,3,3-Trifluoro-1-[3-(4-fluoro-phenyl)-5-methyl-5,6-dihydro-8H-imidazo[1,5-a]pyrazin-7-yl]-2-hydroxy-2-methyl-propan-1-one Compound 52.6 (606.0 mg; 2.619 mmol) was coupled with (R)-3,3,3-trifluoro-2-hydroxy-2-methyl-propionic acid as described for example 9 (step 9.4). Yield: 576 mg (59%) yellow oil The preparative separation of the diastereomers ("A52" and "A53") was performed by SFC (column: ChiralPak AD-H; eluent: CO$_2$:methanol-80:20). The combined fractions were evaporated to dryness.

"A52": 58 mg colorless solid; LC/MS, Rt: 1.45 min; (M+H) 372.1; $^1$H NMR (400 MHz, DMSO-d$_6$, 90° C.) δ 7.76-7.68 (m, 2H), 7.32-7.24 (m, 2H), 7.03 (s, 1H), 6.92 (s, 1H), 5.51-5.23 (m, 1H), 4.81-4.72 (m, 1H), 4.63 (d, J=16.5 Hz, 1H), 4.55 (d, J=13.7 Hz, 1H), 3.63-3.53 (m, 1H), 1.60 (s, 3H), 1.08 (d, J=6.5 Hz, 3H).

"A53": 57 mg colorless solid; LC/MS, Rt: 1.43 min; (M+H) 372.1; $^1$H NMR (400 MHz, DMSO-d$_6$, 90° C.) δ 7.74-7.67 (m, 2H), 7.31-7.22 (m, 2H), 6.98 (s, 1H), 6.86 (s, 1H), 5.43-5.16 (m, 1H), 4.80-4.72 (m, 1H), 4.64 (d, J=16.4 Hz, 1H), 4.51-4.44 (m, 1H), 3.59 (d, J=12.1 Hz, 1H), 1.58 (s, 3H), 1.08 (d, J=6.5 Hz, 3H).

Example 54

(R)-1-[(R)-3-(2,4-Difluoro-phenyl)-5-methyl-5,6-dihydro-8H-imidazo[1,5-a]pyrazin-7-yl]-3,3,3-trifluoro-2-hydroxy-2-methyl-propan-1-one ("A54")

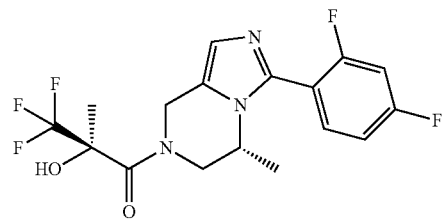 [SMILES: C[C@@H]1CN(C(=O)[C@@](C)(O)C(F)(F)F)Cc2cnc(-c3ccc(F)cc3F)n21]

Example 55

(R)-1-[(S)-3-(2,4-Difluoro-phenyl)-5-methyl-5,6-dihydro-8H-imidazo[1,5-a]pyrazin-7-yl]-3,3,3-trifluoro-2-hydroxy-2-methyl-propan-1-one ("A55")

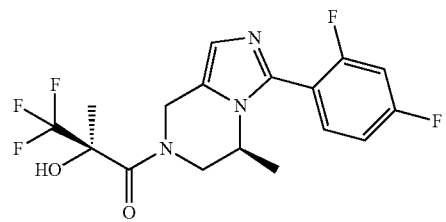 [SMILES: C[C@H]1CN(C(=O)[C@@](C)(O)C(F)(F)F)Cc2cnc(-c3ccc(F)cc3F)n21]

Preparation as described for "A52"/"A53" (steps 52.4-52.7). The preparative separation of the diastereomers was performed by SFC (column: ChiralPak AD-H; eluent: CO$_2$:ethanol-88:12). The combined fractions were evaporated to dryness.

"A54": 333 mg colorless solid; LC/MS, Rt: 1.44 min; (M+H) 390.2; $^1$H NMR (400 MHz, DMSO-d$_6$, 90° C.) δ 7.62-7.50 (m, 1H), 7.30 (td, J=10.2, 2.5 Hz, 1H), 7.18 (td, J=8.4, 2.3 Hz, 1H), 7.03 (s, 1H), 6.89 (s, 1H), 5.34 (br, 1H), 4.68 (d, J=16.3 Hz, 1H), 4.51-4.32 (m, 2H), 3.62 (d, J=11.8 Hz, 1H), 1.59 (s, 3H), 0.99 (d, J=6.3 Hz, 3H).

"A55": 342 mg colorless solid; LC/MS, Rt: 1.42 min; (M+H) 390.2; $^1$H NMR (400 MHz, DMSO-d$_6$, 90° C.) δ 7.67-7.46 (m, 1H), 7.30 (td, J=10.2, 2.5 Hz, 1H), 7.18 (td, J=8.5, 2.4 Hz, 1H), 7.00 (s, 1H), 6.91 (s, 1H), 5.29 (br, 1H), 4.69 (d, J=16.5 Hz, 1H), 4.46-4.31 (m, 2H), 3.66 (d, J=10.1 Hz, 1H), 1.58 (s, 3H), 1.00 (d, J=6.4 Hz, 3H).

Example 56

(R)-1-[(S)-3-(3,5-Difluoro-pyridin-2-yl)-5-methyl-5,6-dihydro-8H-imidazo[1,5-a]pyrazin-7-yl]-3,3,3-trifluoro-2-hydroxy-2-methyl-propan-1-one ("A56")

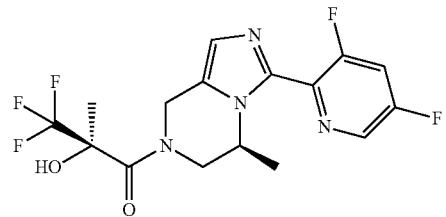 [SMILES: C[C@H]1CN(C(=O)[C@@](C)(O)C(F)(F)F)Cc2cnc(-c3ncc(F)cc3F)n21]

Example 57

(R)-1-[(R)-3-(3,5-Difluoro-pyridin-2-yl)-5-methyl-5,6-dihydro-8H-imidazo[1,5-a]pyrazin-7-yl]-3,3,3-trifluoro-2-hydroxy-2-methyl-propan-1-one ("A57")

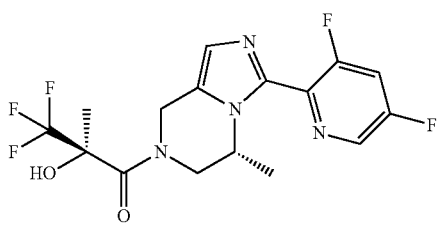 [SMILES: C[C@@H]1CN(C(=O)[C@@](C)(O)C(F)(F)F)Cc2cnc(-c3ncc(F)cc3F)n21]

Preparation as described for "A52"/"A53" (steps 52.4-52.7). The preparative separation of the diastereomers was performed by SFC (column: ChiralPak AD-H; eluent: $CO_2$: ethanol (containing 0.5% diethylamine)-88:12). The combined fractions were evaporated to dryness.

"A56": 333 mg colorless solid; LC/MS, Rt: 1.43 min; (M+H) 391.1; $^1$H NMR (400 MHz, DMSO-$d_6$, 90° C.) δ 8.54 (s, 1H), 8.04-7.82 (m, 1H), 7.11-6.90 (m, 2H), 5.35 (s, br, 1H), 5.15-5.01 (m, 1H), 4.70 (d, J=16.8 Hz, 1H), 4.49 (d, J=13.6 Hz, 1H), 3.60 (d, J=12.4 Hz, 1H), 1.62-1.56 (m, 3H), 1.17 (d, J=6.5 Hz, 3H).

"A57": 342 mg colorless solid; LC/MS, Rt: 1.45 min; (M+H) 391.1; $^1$H NMR (400 MHz, DMSO-$d_6$, 90° C.) δ 8.54 (d, J=2.3 Hz, 1H), 7.99-7.87 (m, 1H), 7.04 (s, 1H), 6.95 (s, 1H), 5.41 (s, br, 1H), 5.17-5.00 (m, 1H), 4.68 (d, J=16.7 Hz, 1H), 4.56 (d, J=13.9 Hz, 1H), 3.55 (d, J=12.8 Hz, 1H), 1.61 (s, 3H), 1.17 (d, J=6.4 Hz, 3H).

Pharmacological Data

TABLE 1

Inhibition of PDHK of some representative compounds of the formula Ia or Ib

| Compound No. | $IC_{50}$ PDHK2 (enzyme assay) | Binding (ITC) KD | $IC_{50}$ (cell data) |
|---|---|---|---|
| "A1" | A | A | C |
| "A2" | C | B | |
| "A3" | A | A | B |
| "A4" | A | A | B |
| "A5" | A | A | B |
| "A6" | B | A | C |
| "A7" | A | A | B |
| "A8" | B | B | C |
| "A9" | A | A | A |
| "A10" | A | A | A |
| "A11" | C | B | B |
| "A12" | A | A | A |
| "A13" | B | B | C |
| "A14" | A | A | A |
| "A15" | B | | B |
| "A16" | A | A | A |
| "A17" | B | B | B |
| "A18" | A | A | A |
| "A19" | B | | B |
| "A20" | A | A | A |
| "A21" | B | | |
| "A22" | A | A | A |
| "A23" | C | | |
| "A24" | A | A | A |
| "A25" | B | | |
| "A26" | C | | |
| "A27" | B | | |
| "A28" | B | A | C |
| "A29" | B | B | |
| "A30" | A | A | A |
| "A31" | C | | |
| "A32" | A | A | A |
| "A33" | C | | |
| "A34" | A | A | A |
| "A35" | B | | |
| "A36" | B | | |
| "A37" | B | B | C |
| "A38" | A | A | A |
| "A39" | B | | |
| "A40" | A | A | A |
| "A41" | C | | |
| "A42" | B | A | |
| "A43" | B | A | B |
| "A44" | B | A | C |
| "A45" | B | A | C |
| "A46" | B | A | C |
| "A47" | B | A | C |
| "A48" | B | A | |
| "A49" | B | A | C |
| "A50" | B | A | C |
| "A51" | B | A | C |
| "A52" | A | A | A |
| "A53" | C | | |
| "A54" | A | A | A |
| "A55" | B | | |
| "A56" | C | | |
| "A57" | B | A | A |

$IC_{50}$: <0.3 μM = A 0.3-3 μM = B 3-50 μM = C

The compounds shown in Table 1 are preferred compounds according to the invention.

Particularly preferred compounds are 14, 20, 34, 38, 40, 54 and 57.

The following examples relate to medicaments:

Example A: Injection Vials

A solution of 100 g of an active ingredient of the formula Ia or Ib and 5 g of disodium hydrogenphosphate in 3 l of bidistilled water is adjusted to pH 6.5 using 2 N hydrochloric acid, sterile filtered, transferred into injection vials, lyophilised under sterile conditions and sealed under sterile conditions. Each injection vial contains 5 mg of active ingredient.

Example B: Suppositories

A mixture of 20 g of an active ingredient of the formula Ia or Ib with 100 g of soya lecithin and 1400 g of cocoa butter is melted, poured into moulds and allowed to cool. Each suppository contains 20 mg of active ingredient.

Example C: Solution

A solution is prepared from 1 g of an active ingredient of the formula Ia or Ib, 9.38 g of $NaH_2PO_4 \cdot 2H_2O$, 28.48 g of $Na_2HPO_4 \cdot 12H_2O$ and 0.1 g of benzalkonium chloride in 940 ml of bidistilled water. The pH is adjusted to 6.8, and the solution is made up to 1 l and sterilised by irradiation. This solution can be used in the form of eye drops.

Example D: Ointment 500 mg of an active ingredient of the formula Ia or Ib are mixed with 99.5 g of Vaseline under aseptic conditions.

Example E: Tablets

A mixture of 1 kg of active ingredient of the formula Ia or Ib, 4 kg of lactose, 1.2 kg of potato starch, 0.2 kg of talc and 0.1 kg of magnesium stearate is pressed in a conventional manner to give tablets in such a way that each tablet contains 10 mg of active ingredient.

Example F: Dragees

Tablets are pressed analogously to Example E and subsequently coated in a conventional manner with a coating of sucrose, potato starch, talc, tragacanth and dye.

Example G: Capsules 2 kg of active ingredient of the formula Ia or Ib are introduced into hard gelatine capsules in a conventional manner in such a way that each capsule contains 20 mg of the active ingredient.

Example H: Ampoules

A solution of 1 kg of active ingredient of the formula Ia or Ib in 60 l of bidistilled water is sterile filtered, transferred into ampoules, lyophilised under sterile conditions and sealed under sterile conditions. Each ampoule contains 10 mg of active ingredient.

The invention claimed is:
1. A compound of formula Ib

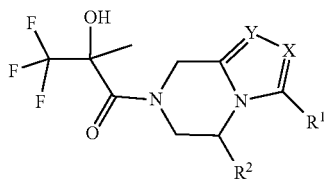

in which
X denotes CH or N,
Y denotes CH or N,
$R^1$ denotes H, A, $(CH_2)_n$Ar, $(CH_2)_n$Het or Cyc,
$R^2$ denotes H or $CH_3$,
Ar denotes phenyl, which is unsubstituted or mono-, di-, tri-, tetra- or pentasubstituted by Hal, A, CN, OA, $[C(R^5)_2]_p$OH, $[C(R^5)_2]_p$N$(R^5)_2$, $NO_2$, $[C(R^5)_2]_p$COOR$^5$, NR$^5$COA, NR$^5$SO$_2$A, $[C(R^5)_2]_p$SO$_2$N$(R^5)_2$, S(O)$_n$A, O$[C(R^5)_2]_m$N$(R^5)_2$, NR$^5$COOA, NR$^5$CON$(R^5)_2$ and/or COA,
Het denotes a mono- or bicyclic saturated, unsaturated or aromatic heterocycle having 1 to 4 N, O and/or S atoms, which is unsubstituted or mono- or disubstituted by Hal, A, CN, OA, $[C(R^5)_2]_p$OH, $[C(R^5)_2]_p$N$(R^5)_2$, $NO_2$, $[C(R^5)_2]_p$COOR$^5$, NR$^5$COA, NR$^5$SO$_2$A, $[C(R^5)_2]_p$SO$_2$N$(R^5)_2$, S(O)$_n$A, O$[C(R^5)_2]_m$N$(R^5)_2$, NR$^5$COOA, NR$^5$CON$(R^5)_2$ and/or COA,
Cyc denotes cyclic alkyl with 3, 4, 5, 6 or 7 C-atoms, which is unsubstituted or monosubstituted by OH,
A denotes unbranched or branched alkyl with 1-10 C-atoms, wherein one or two non-adjacent CH- and/or CH$_2$-groups may in each case be replaced by N-, O- or S-atoms and/or wherein 1-7 H-atoms may each be replaced by $R^4$,
$R^4$ denotes F, Cl or OH,
$R^5$ denotes H or A',
A' denotes unbranched or branched alkyl with 1-6 C-atoms, wherein 1-5 H-atoms may each be replaced by F,
Hal denotes F, Cl, Br or I,
m denotes 1, 2, 3 or 4,
n denotes 0, 1 or 2,
p denotes 0, 1, 2, 3 or 4,
with the proviso that,
if X=CH then Y=N
or
if Y=CH then X=N,
or a pharmaceutically acceptable salt, tautomer, stereoisomer, or mixture thereof in all ratios.

2. A compound according to claim 1, in which
Ar denotes phenyl, which is unsubstituted or mono-, di-, tri-, tetra- or pentasubstituted by Hal, A, CN and/or OA,
or a pharmaceutically acceptable salt, tautomer, stereoisomer, or mixture thereof in all ratios.

3. A compound according to claim 1, in which
Het denotes pyrimidyl, pyridyl, pyridazinyl, pyrazinyl, piperidinyl, pyrrolidinyl, pyrazolyl, thiazolyl, imidazolyl, furanyl, thiophenyl, pyrrolyl, oxazolyl, isoxazolyl, triazolyl, oxadiazolyl or thiadiazolyl, each of which is unsubstituted or mono- or disubstituted by Hal, A and/or OA,
or a pharmaceutically acceptable salt, tautomer, stereoisomer, or mixture thereof in all ratios.

4. A compound according to claim 1 in which
$R^1$ denotes H, A, $(CH_2)_n$Ar, $(CH_2)_n$Het or Cyc,
$R^2$ denotes H or $CH_3$,
Ar denotes phenyl, which is unsubstituted or mono-, di-, tri-, tetra- or pentasubstituted by Hal, A, CN and/or OA,
Het denotes pyrimidyl, pyridyl, pyridazinyl, pyrazinyl, piperidinyl, pyrrolidinyl, pyrazolyl, thiazolyl, imidazolyl, furanyl, thiophenyl, pyrrolyl, oxazolyl, isoxazolyl, triazolyl, oxadiazolyl or thiadiazolyl, each of which is unsubstituted or mono- or disubstituted by Hal, A and/or OA,
Cyc denotes cyclic alkyl with 3, 4, 5, 6 or 7 C-atoms, which is unsubstituted or monosubstituted by OH,
A denotes unbranched or branched alkyl with 1-10 C-atoms, wherein one or two non-adjacent CH- and/or CH$_2$-groups may in each case be replaced by N-, O- or S-atoms and/or wherein 1-7 H-atoms may each be replaced by $R^4$,
$R^4$ denotes F, Cl or OH,
Hal denotes F, Cl, Br or I,
n denotes 0, 1 or 2,
or a pharmaceutically acceptable salt, tautomer, stereoisomer, or mixture thereof in all ratios.

5. A process for the preparation of compounds according to claim 1, said process comprising:
reacting a compound of the formula IIb

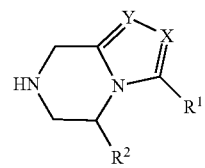

in which X, Y, $R^1$ and $R^2$ have the meanings indicated in claim 1, with a compound of formula III

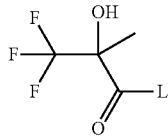

in which L denotes Cl, Br, I or a free or reactively functionally modified OH group, and/or a base or acid of the formula Ib is converted into one of its salts.

6. A pharmaceutical composition comprising at least one compound according to claim 1, and optionally a pharmaceutically acceptable carrier, excipient or vehicle.

7. A compound according to claim 1, wherein X denotes N and Y denotes N.

8. A compound according to claim 1, wherein X denotes CH and Y denotes N.

9. A compound according to claim 1, wherein X denotes N and Y denotes CH.

10. A compound according to claim 1, wherein said compound is a pharmaceutically acceptable salt, tautomer, stereoisomer, or mixture thereof in all ratios, of a compound of formula Ib.

11. A compound according to claim 1, wherein A denotes methyl, ethyl, propyl, isopropyl, butyl, isobutyl, sec-butyl, tert-butyl, pentyl, hexyl, trifluoromethyl, pentafluoroethyl, 1,1,1-trifluoroethyl, $CH_2OCH_3$, $CH_2CH_2OH$ or $CH_2CH_2OCH_3$.

12. A compound according to claim 1, wherein Cyc denotes cyclopropyl, cyclobutyl, cyclopentyl, cyclohexyl or cycloheptyl, which in each case is unsubstituted or monosubstituted by OH.

13. The compound according to claim 1, wherein the compound is ((R)-3,3,3-Trifluoro-1-[(R)-3-(4-fluoro-phenyl)-5-methyl-5,6-dihydro-8H-imidazo[1,5-a]pyrazin-7-yl]-2-hydroxy-2-methyl-propan-1-one), or a pharmaceutically acceptable salt, tautomer, stereoisomer, or mixture thereof in all ratios.

14. A compound according to claim 1, selected from the group

| No. | Name |
|---|---|
| "A48" | (R)-3,3,3-Trifluoro-2-hydroxy-2-methyl-1-(3-phenyl-5,6-dihydro-8H-[1,2,4]¬tri¬azolo¬[4,3-a]pyrazin-7-yl)-propan-1-one |

| No. | Name |
|---|---|
| "A49" | (R)-3,3,3-Trifluoro-2-hydroxy-2-methyl-1-(3-phenyl-5,6-dihydro-8H-imidazo[1,2-a]pyrazin-7-yl)-propan-1-one |
| "A50" | (R)-3,3,3-Trifluoro-2-hydroxy-2-methyl-1-(3-phenyl-5,6-dihydro-8H-imi¬dazo¬[1,5-a]pyrazin-7-yl)-propan-1-one |
| "A51" | (R)-3,3,3-Trifluoro-1-[3-(4-fluoro-phenyl)-5,6-dihydro-8H-imidazo[1,5-a]pyra¬zin-7-yl]-2-hydroxy-2-methyl-propan-1-one |
| "A52" | (R)-3,3,3-Trifluoro-1-[(R)-3-(4-fluoro-phenyl)-5-methyl-5,6-dihydro-8H-imi¬dazo[1,5-a]pyrazin-7-yl]-2-hydroxy-2-methyl-propan-1-one |
| "A53" | (R)-3,3,3-Trifluoro-1-[(S)-3-(4-fluoro-phenyl)-5-methyl-5,6-dihydro-8H-imi¬dazo[1,5-a]pyrazin-7-yl]-2-hydroxy-2-methyl-propan-1-one |
| "A54" | (R)-1-[(R)-3-(2,4-Difluoro-phenyl)-5-methyl-5,6-dihydro-8H-imidazo[1,5-a]pyrazin-7-yl]-3,3,3-trifluoro-2-hydroxy-2-methyl-propan-1-one |
| "A55" | (R)-1-[(S)-3-(2,4-Difluoro-phenyl)-5-methyl-5,6-dihydro-8H-imidazo[1,5-a]pyrazin-7-yl]-3,3,3-trifluoro-2-hydroxy-2-methyl-propan-1-one |
| "A56" | (R)-1-[(S)-3-(3,5-Difluoro-pyridin-2-yl)-5-methyl-5,6-dihydro-8H-imidazo¬[1,5-a]pyrazin-7-yl]-3,3,3-trifluoro-2-hydroxy-2-methyl-propan-1-one |
| "A57" | (R)-1-[(R)-3-(3,5-Difluoro-pyridin-2-yl)-5-methyl-5,6-dihydro-8H-imidazo¬[1,5-a]pyrazin-7-yl]-3,3,3-trifluoro-2-hydroxy-2-methyl-propan-1-one | or a pharmaceutically acceptable salt, tautomer, stereoisomer, or mixture thereof in all ratios.

15. A compound according to claim 1, selected from the group

| No. | Name |
|---|---|
| "A50" | (R)-3,3,3-Trifluoro-2-hydroxy-2-methyl-1-(3-phenyl-5,6-dihydro-8H-imidazo[1,5-a]pyrazin-7-yl)-propan-1-one, |
| "A51" | (R)-3,3,3-Trifluoro-1-[3-(4-fluoro-phenyl)-5,6-dihydro-8H-imidazo[1,5-a]pyrazin-7-yl]-2-hydroxy-2-methyl-propan-1-one, |
| "A52" | (R)-3,3,3-Trifluoro-1-[(R)-3-(4-fluoro-phenyl)-5-methyl-5,6-dihydro-8H-imidazo[1,5-a]pyrazin-7-yl]-2-hydroxy-2-methyl-propan-1-one, |
| "A53" | (R)-3,3,3-Trifluoro-1-[(S)-3-(4-fluoro-phenyl)-5-methyl-5,6-dihydro-8H-imidazo[1,5-a]pyrazin-7-yl]-2-hydroxy-2-methyl-propan-1-one, |
| "A54" | (R)-1-[(R)-3-(2,4-Difluoro-phenyl)-5-methyl-5,6-dihydro-8H-imidazo[1,5-a]pyrazin-7-yl]-3,3,3-trifluoro-2-hydroxy-2-methyl-propan-1-one, |
| "A55" | (R)-1-[(S)-3-(2,4-Difluoro-phenyl)-5-methyl-5,6-dihydro-8H-imidazo[1,5-a]pyrazin-7-yl]-3,3,3-trifluoro-2-hydroxy-2-methyl-propan-1-one, |
| "A56" | (R)-1-[(S)-3-(3,5-Difluoro-pyridin-2-yl)-5-methyl-5,6-dihydro-8H-imidazo[1,5-a]pyrazin-7-yl]-3,3,3-trifluoro-2-hydroxy-2-methyl-propan-1-one, and |
| "A57" | (R)-1-[(R)-3-(3,5-Difluoro-pyridin-2-yl)-5-methyl-5,6-dihydro-8H-imidazo¬[1,5-a]pyrazin-7-yl]-3,3,3-trifluoro-2-hydroxy-2-methyl-propan-1-one, | or a pharmaceutically acceptable salt, tautomer, stereoisomer, or mixture thereof in all ratios.

* * * * *